(12) United States Patent
Haley et al.

(10) Patent No.: US 9,244,058 B2
(45) Date of Patent: Jan. 26, 2016

(54) BIOLOGICAL MARKERS PREDICTIVE OF ANTI-CANCER RESPONSE TO EPIDERMAL GROWTH FACTOR RECEPTOR KINASE INHIBITORS

(75) Inventors: John D. Haley, Farmingdale, NY (US); Graeme Griffin, Farmingdale, NY (US); Lukas A. Amler, San Francisco, CA (US); David A. Eberhard, San Francisco, CA (US); Robert L. Yauch, San Francisco, CA (US)

(73) Assignee: OSI Pharmaceuticals, LLC, Melville, NY (US)

( * ) Notice: Subject to any disclaimer, the term of this patent is extended or adjusted under 35 U.S.C. 154(b) by 850 days.

(21) Appl. No.: 13/374,132

(22) Filed: Dec. 12, 2011

(65) Prior Publication Data

US 2012/0157480 A1 Jun. 21, 2012

Related U.S. Application Data

(62) Division of application No. 11/377,530, filed on Mar. 16, 2006, now Pat. No. 8,093,011.

(60) Provisional application No. 60/662,545, filed on Mar. 16, 2005, provisional application No. 60/671,821, filed on Apr. 15, 2005.

(51) Int. Cl.
G01N 33/53 (2006.01)
G01N 33/50 (2006.01)
G01N 33/574 (2006.01)

(52) U.S. Cl.
CPC ...... *G01N 33/5011* (2013.01); *G01N 33/57407* (2013.01); *G01N 33/57484* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,617,121 B1 | 9/2003 | Cano Garcia et al. | |
| 7,081,340 B2 | 7/2006 | Baker | |
| 8,093,011 B2 | 1/2012 | Haley | |
| 2004/0106605 A1 | 6/2004 | Carboni | |
| 2004/0132097 A1 | 7/2004 | Bacus | |
| 2004/0209930 A1 | 10/2004 | Carboni | |
| 2005/0019785 A1 | 1/2005 | Baker | |
| 2006/0046249 A1 | 3/2006 | Huang | |
| 2006/0211060 A1 | 9/2006 | Haley | |
| 2007/0065858 A1 | 3/2007 | Haley | |
| 2007/0141621 A1 | 6/2007 | Agus | |
| 2007/0212738 A1 | 9/2007 | Haley | |
| 2007/0270505 A1 | 11/2007 | Bunn | |
| 2008/0085519 A1 | 4/2008 | Gabrin | |
| 2008/0090233 A1 | 4/2008 | Garcia | |
| 2008/0312260 A1 | 12/2008 | Haley | |

FOREIGN PATENT DOCUMENTS

| | | | |
|---|---|---|---|
| WO | 03078662 A1 | | 9/2003 |
| WO | 2004046386 A1 | | 6/2004 |
| WO | 2004063709 A2 | | 7/2004 |
| WO | 2004065602 A1 | | 8/2004 |
| WO | 2004071572 A2 | | 8/2004 |
| WO | 2004111273 A2 | | 12/2004 |
| WO | 2005017493 A2 | | 2/2005 |
| WO | 2005067667 A2 | | 7/2005 |
| WO | 2005070020 A2 | | 8/2005 |
| WO | WO 2005/070020 | * | 8/2005 |
| WO | 2005094332 A2 | | 10/2005 |
| WO | 2005099363 A2 | | 10/2005 |
| WO | 2005107803 A2 | | 11/2005 |
| WO | 2005117553 A2 | | 12/2005 |
| WO | 2006099396 A2 | | 9/2006 |
| WO | 2006101925 A2 | | 9/2006 |
| WO | 2007028146 A2 | | 3/2007 |
| WO | 2007035744 A1 | | 3/2007 |
| WO | 2007075554 A2 | | 7/2007 |
| WO | 2008127718 A2 | | 10/2008 |
| WO | 2010120966 A1 | | 10/2010 |

OTHER PUBLICATIONS

Matar et al (Clinical Cancer Research, 2004, 10:6487-6501).*
Perez-Soler et al (Clinical Cancer Research, 2004, 15:4238s-4240s).*
Natale et al (Proc Am Soc Clin Oncol, 2003).*
Yang et al (Journal of Clinical Oncology, 2004, ASCO Annual Meeting Proceedings, vol. 22, No. 14S (July Suppl):abstract #577).*
Yang et al (Clinical Cancer Research, 2005, 11:6226-6232).*
Yang et al (Clinical Cancer Research, 2005, 11:6226-6232) Supplementary Table 1.*

(Continued)

*Primary Examiner* — Laura B Goddard
(74) *Attorney, Agent, or Firm* — Brinks Gilson & Lione

(57) ABSTRACT

The present invention provides diagnostic and prognostic methods for predicting the effectiveness of treatment of a cancer patient with an EGFR kinase inhibitor. Methods are provided for predicting the sensitivity of tumor cell growth to inhibition by an EGFR kinase inhibitor, comprising assessing whether the tumor cell has undergone an epithelial to mesenchymal transition (EMT), by determining the expression level of epithelial and/or mesenchymal biomarkers, wherein tumor cells that have undergone an EMT are substantially less sensitive to inhibition by EGFR kinase inhibitors. Improved methods for treating cancer patients with EGFR kinase inhibitors that incorporate the above methodology are also provided. Additionally, methods are provided for the identification of new biomarkers that are predictive of responsiveness of tumors to EGFR kinase inhibitors. Furthermore, methods for the identification of agents that restore the sensitivity of tumor cells that have undergone EMT to inhibition by EGFR kinase inhibitors are also provided.

6 Claims, 9 Drawing Sheets
(5 of 9 Drawing Sheet(s) Filed in Color)

(56) References Cited

OTHER PUBLICATIONS

Sarrio, D., et al. (2008) Cancer Research 68:4, 989-997.
Savagner, P. (2001) Bioessays 23:912-923.
Schaafsma, H.E., et al. (May 1993) J. Pathol. 170(1): 77-86.
Schlessinger, K., et al. (2004) Nature Cell Biology 6(10):913-915.
Schussler, M.H., et al. (Mar. 1992) Am. J. Pathol. 140(3): 559-568.
Shrader, M., et al. (2007) Mol Cancer Ther 6(1): 277-285.
Shen, X., et al. (2004) Amer J Path 165 (4): 1315-1329.
"Sternberg, D., TAT Meeting, 8th International Symposium on Targeted Anticancer Therapies, Mar. 4-6, 2010. Bethesda, MD, USA, "The Development and Application of EMT Biomarkers in the Therapy of Solid Tumors"; 37 slides."
Struz, F., et al. (2002) Kidney Interantional 61:1714-1728.
Sun, T.T., et al. (1984) Cancer Cell 1, The Transformed Phonotype vol. 1; 169-176, Levine, A. et al. eds.; Cold Spring Harbor Laboratory.
Suto, K., et al. (1999) J. Can.Res.Clin. Oncol. 125:83-88.
Takenaka, K., et al. (2005) Cancer Epidemiology Biomakers & Prevention 14(8) :1972-1975.
Tejeda, M.L., et al. (2006) Clinical Cancer Research 12(9): 2676-2688, May 1, 2006.
Thiery, J.P. (2002) Nat. Rev. Cancer 2:442-454.
Thomas, P.A., et al. (1999) Clinical Cancer Research 5: 2698-2703, Oct. 1999.
Thomson, S., et al. (2005) Cancer Res. 65(20):9455-9462.
Tuma, R.S., et al. (2005) J. Natl. Cancer Institute, 97(14):1028-1029.
Turley, E.A., et al. (2008) Nature Clinical Practice 5(5): 280-290.
Umemoto, M., et al. (2001) Brit. J. Can. 85:1032-1036.
Valdes, F., et al. (2002) Molecular Cancer Research, 1:68-78.
Valles, A. M., et al. (1990) Proc. Natl. Acad. Sci. USA 87:1124-1128, Feb. 1990, Cell Biology.
Wilding, J., et al. (1996) Cancer Res 56: 5285-5292.
Witta S.E, et al. (2004) Proc. Amer. Assoc. Cancer Res. vol. 45 Abst. #3671, pp. 1-2.
Witta S.E. et al. (2005) J. Clin. Oncol. vol. 23, No. 165 (Jun. 1 Suppl.) Abst. #7083 (ASCO Proceedings).
Witta, S.E., et al. (2006) Cancer Res. 66(2):944-950.
Written Opinion of the International Search Authority in PCT/US2008/004819.
Xie, L., et al. (2004) Neoplasia 6(5): 603-610.
Yang, L., et al. (2006) Cell 127:139-155.
Yano, S. et al. (2003) AntiCancer Res. 23(5A):3639-3650.
Yausch, R. L., et al. (2005) Clin. Cancer Res. 11:8686-8698.
Younes, M. (2005) J. Clinical Oncology 23(4): 923-924.
Zavadil, J., et al. (2005) Oncogene 24:5764-5774.
Answers.com definition for "tumor", p. 1 (Apr. 17, 2009).
International Search Report in PCT/US2006/009403, 2006.
International Search Report in PCT/US2010/031144, 2010.
International Search Report in PCT/US2008/004818, 2008.
International Search Report of the International Search Authority in PCT/US2008/004819, 2008.
International Preliminary Report on Patentability and Written Opinion in PCT/US2006/009403, 2006.
International Preliminary Report on Patentability and Written Opinion in PCT/US2008/004818, 2008.
International Preliminary Report on Patentability and Written Opinion of the International Searching Authority in PCT/US2010/031144, 2010.
Aigner, K. et al. (2007) Oncogene pp. 1-10, Nature Publishing Group.
Amman, J. et al. (2005) Cancer Res. 65(1):226-235.
Andl, C. D., et al (2005) Cancer Biology and Therapy 4(1): 28-31.
Andl, C. D., et al (2003) J Biol Chem, 278 (No. 3):1824-1830.
ATCC search Calu 6 (pp. 1-3; Mar. 10, 2010), 2010.
ATCC search H1703 (pp. 1-3; Mar. 10, 2010), 2010.
ATCC search H292 (pp. 1-3; Mar. 10, 2010)—2010.
ATCC search H358 (pp. 1-3; Mar. 10, 2010), 2010.
Auersperg, N. et al (1999) Proc Natl Acad Sci 96:6249-6254.
Babiychuk, E B et al. (2002) Bichimica ET Biophysica ACTA (BBA)—Proteins & Proteomics, Elsevier 1600, No. 1-2: 154-161.
Bailey, L.R. et al. (2003) Proc. Am. Assoc. Res. 44:1362. abst. LB-170.
Bankfalvi, A., et al (2002) J Oral Pathol Med 31: 450-457.
Barrallo-Gimeno, A. et al. (2005) Development 132:3151-3161.
Bates, R.C. et al. (2003) Current Biology 13 pp. 1721-1727.
Bergh, J., et al. (1984) Expression of intermediate filaments in established human lung cancer cell lines. An indicator of differentiation and derivation Lab Invest 51(3): 307-316.
Bianco, R. et al. (2005) Endocrine-related cancer 12:S159-S171.
Biowww.net; "BRK gene" definition; pp. 1-3; Mar. 9, 2010.
Brehmer, D. et al; (2005) Cancer Res. 65(2):379-382.
Broers, J.L.V. et al. (1986) Journal of Cell Science 83: 37-60.
Broers, J.L.V. et al. (1988) Journal of Cell Science 91: 91-108.
Buck, E. et al. (2007) Molecular Cancer Therapeutics 6(2): 532-541.
Buck, E. et al. (2006) Molecular Cancer Therapeutics 5(8): 2051-2059.
Camp, E.R. et al. (2005) Clinical Cancer Research (1):397-405.
Cano, A. et al; (2000) Nature Cell Biology 2: 76-83.
Castillo, L. et al. (2004) Annals of Oncology 15:1007-1012.
Chaffer, C. L., et al. (2006) Cancer Research 66(23): 11271-11278.
Chandler, L.A., et al. (1999) Int. J. Cancer 82: 451-458.
Christofori, G. (2006) Nature 441(7092): 444-450.
Chung, L.W.K., et al. (2005) The Journal of Urology 173:10-20.
Ciruna, B., et al. (2001) Developmental Cell 1:37-49.
Clara, M., et al. (2007) European Journal of Cancer Supplement 5:4, 366-367.
Clark, D. M., et al. (1991) Histochemistry 96:5, 405-412.
Coltrera, M.D., et al. (1995) Cancer Research 55: 2703-2708.
Dai, Q., et al. (2005) Clinical Cancer Research 11:1572-1578.
Dancey, J. and Sausville, E.A. (2003) Nature Rev. Drug Discovery 2:296-313.
Dandachi, N., et al. (2001) J. Pathology; 193:181-189.
De Bono, J.S. and Rowinsky, E.K. (2002) Trends in Mol. Medicine 8:S19-S26.
De Craene, B., et al. (2005) Cancer Res. 65(14): 6237-6244.
Derwent/Delphion record for WO 2004065602.
D'Souza, B., et al. (1994) Proc Natl Acad Sci 91:7202-7206.
Dumstrei, K., et al. (2002) Development 129: 3983-3994.
Ei-Deiry, W.S., et al. (2005) Cancer Res. 65(11):4475-4484.
Fedor-Chaiken, M., et al. (2003) Cell Communication and Adhesion 10:105-118.
Frederick, B.A., et al. (2007) Mol Cancer Ther 6(6): 1683-1691.
Giaccone, G. (2005) Annals of Oncology 16: 538-548.
Grande, M., et al. (2002) J. Cell Science 115:4227-4236.
Grille S.J. et al. (2003) Cancer Research 63, 2172-2178.
Gura, T. (1997) Science 278: 1041-1042.
Hazan, R. B. and Norton, L. (1998) J Biol Chem 273 (15), 9078-9084.
Hirsch, F.R. and Witta, S. (2005) Curr. Opin. Oncol. 17:118-122.
Hoorens, A., et al. (1998 May) J. Pathol. 185(1): 53-60.
Huber, M., et al. (2005) Current Opinion in Cell Biology 17:548-558.
Jain, A., et al. (2005) PNAS 102(33): 11858-11863.
Janda, E., et al. (2002) J. Cell Biology 156(2):299-313.
Jawhari, A. U., et al. (1999) J Pathol 187: 155-157.
Jechlinger, M., et al. (2006) The Journal of Clinical Investigation, http: www.jci.org, vol. 116(6): 1561-1570.
Jechlinger, M., et al. (2003) Oncogene 22: 7155-7169.
Jiao, W., et al. (2002) British of Journal Cancer 86: 98-101.
Kamalati, T., et al. (2000) Oncogene 19:5471-5476.
Kamalati, T., et al. (1996) J. Biol. Chemistry 271(48):30956-30963.
Kang, Y., et al. (2004) Cell 118(3):277-279.
Kassouf, W., et al. (2005) Cancer Res. 65(2):10524-10535.
Kiermer, A.K., et al. (2001) Oncogene 20:6679-6688.
Kim, K.S., et al. (2005) Clinical Cancer Research, 11:2244-2251.
Kobayashi, S., et al. (2005) New England Journal of Medicine 352:786-792.
Kokubo, Y., et al. (2005) British J. Cancer 92:1711-1719.
Kris, M., et al. (2003) JAMA 290 (16):2149-2158.
Laasko, M., et al. (2006) Clinical Cancer Research: An official Journal of the American Association for Cancer Research 12: 14 part 1, 4185-4191.
Lan, M., et al. (2004) Carcinogenesis 25(12): 2385-2395.
Lee, J. M., et al. (2006) Journal of Cell Biology 172:7, 973-981.

(56) References Cited

OTHER PUBLICATIONS

Lemoine, N.R., et al. (1992) Br. J. Cancer 66:1116-11121.
Letters to Journal (2005) J of Clin. Onco. 23, No. 4, Feb. 1, 2005; pp. 923-924.
Lippman, S.M., et al (2005) Clin. Cancer Res. 11(17):6097-6099.
Lu, Z., et al. (2003) Cancer Cell. 4(6):499-515.
Markl, J. (1991) Journal of Cell Science 98: 261-264.
Matar, P., et al. (2004) Clin. Cancer Res. 10:6487-6501.
Matei, D., et al. (2006) Oncogene 25: 2060-2069.
Miyanaga, Akihiko et al. Oncology Reports, 2008 vol. 19, No. 2 pp. 377-383.
Modern Pharmacology, 1990, Eds. Craig and Stitzel, Publishers, Little, Brown and Company, Chapter 60, pp. 776-778.
Moll, R., et al. (1982) Cell 31: 11-24.
Moody, S.E., et al. (2005) Cancer Cell vol. 8, Sep. 2005, pp. 197-209.
Moon, H., et al. (2001) Gynecologic Oncology 81:355-359.
Nunes, M., et al. (2004) Molecular Cancer Therapeutics, 3(1):21-27.
Ohira, T., et al. (2003) PNAS 100(18):10429-10434.
Oshima, R.G. (2002) Cell Death and Differentiation 9: 486-492.
Pece, S., et al. (275) J Biol Chem 275 (52): 41227-41233.
Perez-Solar, R., et al. (2003) Lung Cancer 41 (Suppl. 2), p. S72, Abstract O247.
Qian, X., et al. (2004) EMBO 23:1739-1748.
Ramaekers, F.C.S., et al. (1987) Acta Histochemica Suppl. 34: 45-56.
Ramaekers, F.C.S., et al. (1983) Proc. Natl. Acad. Sci. USA 80: 2618-2622, May 1983, Cell Biology.
Richardson, F., et al. (2009) International Association for the Study of Lung Cancer, 13th World Conference on Lung Cancer, Jul. 31-Aug. 4, 2009, Moscone West, San Francisco, USA. "Comparison of E-cadherin IHC Status with Clinical Outcomes from Erlotinib in the Non Small Cell Lung Cancer (NSCLC) Clinical Trial NCIC CTG BR.21" e-Poster: PD7.2.5. Congress: WCLC 2009; 29 pages.
Sabbah, M. et al. (2008) Drug Resistance Updates 11:123-151.
Sakurai, H., et al. (1997) Proc. Natl. Acad. Sci. USA, 94:6279-6284.

\* cited by examiner

A.

B.

BIOLOGICAL MARKERS PREDICTIVE OF ANTI-CANCER RESPONSE TO EPIDERMAL GROWTH FACTOR RECEPTOR KINASE INHIBITORS

CROSS-REFERENCE TO RELATED APPLICATIONS

This application is a divisional application of U.S. application Ser. No. 11/377,530, filed Mar. 16, 2006, now U.S. Pat. No. 8,093,011 which claims the benefit of U.S. Provisional Application No. 60/662,545, filed Mar. 16, 2005, and U.S. Provisional Application No. 60/671,821, filed Apr. 15, 2005, all of which are herein incorporated by reference in their entirety.

BACKGROUND OF THE INVENTION

The present invention is directed to methods for diagnosing and treating cancer patients. In particular, the present invention is directed to methods for determining which patients will most benefit from treatment with an epidermal growth factor receptor (EGFR) kinase inhibitor.

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA™) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors, but do not identify a completely non-responsive phenotype.

The development for use as anti-tumor agents of compounds that directly inhibit the kinase activity of the EGFR, as well as antibodies that reduce EGFR kinase activity by blocking EGFR activation, are areas of intense research effort (de Bono J. S. and Rowinsky, E. K. (2002) Trends in Mol. Medicine. 8:S19-S26; Dancey, J. and Sausville, E. A. (2003) Nature Rev. Drug Discovery 2:92-313). Several studies have demonstrated, disclosed, or suggested that some EGFR kinase inhibitors might improve tumor cell or neoplasia killing when used in combination with certain other anti-cancer or chemotherapeutic agents or treatments (e.g. Herbst, R. S. et al. (2001) Expert Opin. Biol. Ther. 1:719-732; Solomon, B. et al (2003) Int. J. Radiat. Oncol. Biol. Phys. 55:713-723; Krishnan, S. et al. (2003) Frontiers in Bioscience 8, e1-13; Grunwald, V. and Hidalgo, M. (2003) J. Nat. Cancer Inst. 95:851-867; Seymour L. (2003) Current Opin. Investig. Drugs 4(6): 658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Ciardiello, F. et al. (2000) Clin. Cancer Res. 6:2053-2063; and Patent Publication No: US 2003/0157104).

Erlotinib (e.g. erlotinib HCl, also known as TARCEVA™ or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). More recently, erlotinib has demonstrated promising activity in phase I and II trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), CRC (Oza, M., et al. (2003) Proc. Am. Soc. Clin. Oncol. 22:196a, abstract 785) and MBC (Winer, E., et al. (2002) Breast Cancer Res. Treat. 76:5115a, abstract 445). In a phase III trial, erlotinib monotherapy significantly prolonged survival, delayed disease progression and delayed worsening of lung cancer-related symptoms in patients with advanced, treatment-refractory NSCLC (Shepherd, F. et al. (2004) J. Clin. Oncology, 22:14 S (July 15 Supplement), Abstract 7022). While most of the clinical trial data for erlotinib relate to its use in NSCLC, preliminary results from phase I/II studies have demonstrated promising activity for erlotinib and capecitabine/erlotinib combination therapy in patients with wide range of human solid tumor types, including CRC (Oza, M., et al. (2003) Proc. Am. Soc. Clin. Oncol. 22:196a, abstract 785) and MBC (Jones, R. J., et al. (2003) Proc. Am. Soc. Clin. Oncol. 22:45a, abstract 180). In November 2004 the U.S. Food and Drug Administration (FDA) approved TARCEVA™ for the treatment of patients with locally advanced or metastatic non-small cell lung cancer (NSCLC) after failure of at least one prior chemotherapy regimen. TARCEVA™ is the only drug in the epidermal growth factor receptor (EGFR) class to demonstrate in a Phase III clinical trial an increase in survival in advanced NSCLC patients.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as EGFR kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

Target-specific therapeutic approaches, such as erlotinib, are generally associated with reduced toxicity compared with conventional cytotoxic agents, and therefore lend themselves to use in combination regimens. Promising results have been observed in phase I/II studies of erlotinib in combination with bevacizumab (Mininberg, E. D., et al. (2003) Proc. Am. Soc. Clin. Oncol. 22:627a, abstract 2521) and gemcitabine (Dragovich, T., (2003) Proc. Am. Soc. Clin. Oncol. 22:223a, abstract 895). Recent data in NSCLC phase III trials have shown that first-line erlotinib or gefitinib in combination with standard chemotherapy did not improve survival (Gatzemeier, U., (2004) Proc. Am. Soc. Clin. Oncol. 23:617 (Abstract 7010); Herbst, R. S., (2004) Proc. Am. Soc. Clin. Oncol. 23:617 (Abstract 7011); Giaccone, G., et al. (2004) J. Clin. Oncol. 22:777; Herbst, R., et al. (2004) J. Clin. Oncol. 22:785). However, pancreatic cancer phase III trials have shown that first-line erlotinib in combination with gemcitabine did improve survival (OSI Pharmaceuticals/Genentech/Roche Pharmaceuticals Press Release, Sep. 20, 2004).

Several groups have investigated potential biomarkers to predict a patient's response to EGFR inhibitors (see for example, PCT publications: WO 2004/063709, WO 2005/017493, WO 2004/111273, WO 2004/071572, WO 2005/117553 and WO 2005/070020; and US published patent applications: US 2005/0019785, and US 2004/0132097). However, no diagnostic or prognostic tests have yet emerged that can guide practicing physicians in the treatment of their patients with EGFR kinase inhibitors.

During most cancer metastases, an important change occurs in a tumor cell known as the epithelial-mesenchymal transition (EMT) (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). Epithelial cells, which are bound together tightly and exhibit polarity, give rise to mesenchymal cells, which are held together more loosely, exhibit a loss of polarity, and have the ability to travel. These mesenchymal cells can spread into tissues surrounding the original tumor, as well as separate from the tumor, invade blood and lymph vessels, and travel to new locations where they divide and form additional tumors. EMT does not occur in healthy cells except during embryogenesis. Under normal circumstances TGF-β acts as a growth inhibitor. However it is believed that during cancer metastasis, TGF-β begins to promote EMT.

Thus, there remains a critical need for improved methods for determining the best mode of treatment for any given cancer patient and for the incorporation of such determinations into more effective treatment regimens for cancer patients, whether such inhibitors are used as single agents or combined with other anti-cancer agents.

SUMMARY OF THE INVENTION

The present invention provides diagnostic and prognostic methods for predicting the effectiveness of treatment of a cancer patient with an EGFR kinase inhibitor. Based on the surprising discovery that the sensitivity of tumor cell growth to inhibition by EGFR kinase inhibitors is dependent on whether such tumor cells have undergone an EMT, methods have been devised for determining epithelial and/or mesenchymal biomarkers to predict the sensitivity of tumor cells to EGFR kinase inhibitors.

Accordingly, the present invention provides a method of predicting the sensitivity of tumor cell growth to inhibition by an EGFR kinase inhibitor, comprising: assessing the level of an epithelial biomarker expressed by a tumor cell; and predicting the sensitivity of tumor cell growth to inhibition by an EGFR kinase inhibitor, wherein high expression levels of tumor cell epithelial biomarkers correlate with high sensitivity to inhibition by EGFR kinase inhibitors.

The present invention also provides a method of predicting the sensitivity of tumor cell growth to inhibition by an EGFR kinase inhibitor, comprising: assessing the level of a mesenchymal biomarker expressed by a tumor cell; and predicting the sensitivity of tumor cell growth to inhibition by an EGFR kinase inhibitor, wherein high expression levels of tumor cell mesenchymal biomarkers correlate with low sensitivity to inhibition by EGFR kinase inhibitors.

Improved methods for treating cancer patients with EGFR kinase inhibitors that incorporate the above methodology are also provided. Thus, the present invention further provides a method for treating tumors or tumor metastases in a patient, comprising the steps of diagnosing a patient's likely responsiveness to an EGFR kinase inhibitor by assessing whether the tumor cells have undergone an epithelial-mesenchymal transition, and administering to said patient a therapeutically effective amount of an EGFR kinase inhibitor.

Additionally, methods are provided for the identification of new epithelial or mesenchymal biomarkers that are predictive of responsiveness of tumors to EGFR kinase inhibitors.

Thus, for example, the present invention further provides a method of identifying an epithelial biomarker that is diagnostic for more effective treatment of a neoplastic condition with an EGFR kinase inhibitor, comprising: measuring the level of a candidate epithelial biomarker in neoplastic cell-containing samples from patients with a neoplastic condition, and identifying a correlation between the level of said candidate epithelial biomarker in the sample from the patient with the effectiveness of treatment of the neoplastic condition with an EGFR kinase inhibitor, wherein a correlation of high levels of the epithelial biomarker with more effective treatment of the neoplastic condition with an EGFR kinase inhibitor indicates that said epithelial biomarker is diagnostic for more effective treatment of the neoplastic condition with an EGFR kinase inhibitor.

The present invention further provides a method of identifying a mesenchymal biomarker that is diagnostic for less effective treatment of a neoplastic condition with an EGFR kinase inhibitor, comprising: (a) measuring the level of a candidate mesenchymal biomarker in neoplastic cell-containing samples from patients with a neoplastic condition, and (b) identifying a correlation between the level of said candidate mesenchymal biomarker in the sample from the patient with the effectiveness of treatment of the neoplastic condition with an EGFR kinase inhibitor, wherein a correlation of high levels of the mesenchymal biomarker with less effective treatment of the neoplastic condition with an EGFR kinase inhibitor indicates that said mesenchymal biomarker is diagnostic for less effective treatment of the neoplastic condition with an EGFR kinase inhibitor.

Furthermore, methods for the identification of agents that restore the sensitivity of tumor cells that have undergone EMT to inhibition by EGFR kinase inhibitors are also provided. Thus, for example, the present invention provides a method for the identification of an agent that enhances sensitivity of the growth of a tumor cell to an EGFR kinase inhibitor, said tumor cell having being characterized as one that has previously undergone an epithelial-mesenchymal transition, comprising contacting a sample of said tumor cells with an EGFR kinase inhibitor, contacting an identical sample of said tumor cells with an EGFR kinase inhibitor in the presence of a test agent, comparing the EGFR kinase inhibitor-mediated growth inhibition in the presence and absence of the test agent, and determining whether the test agent is an agent that enhances sensitivity of the growth of the tumor cell to an EGFR kinase inhibitor.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
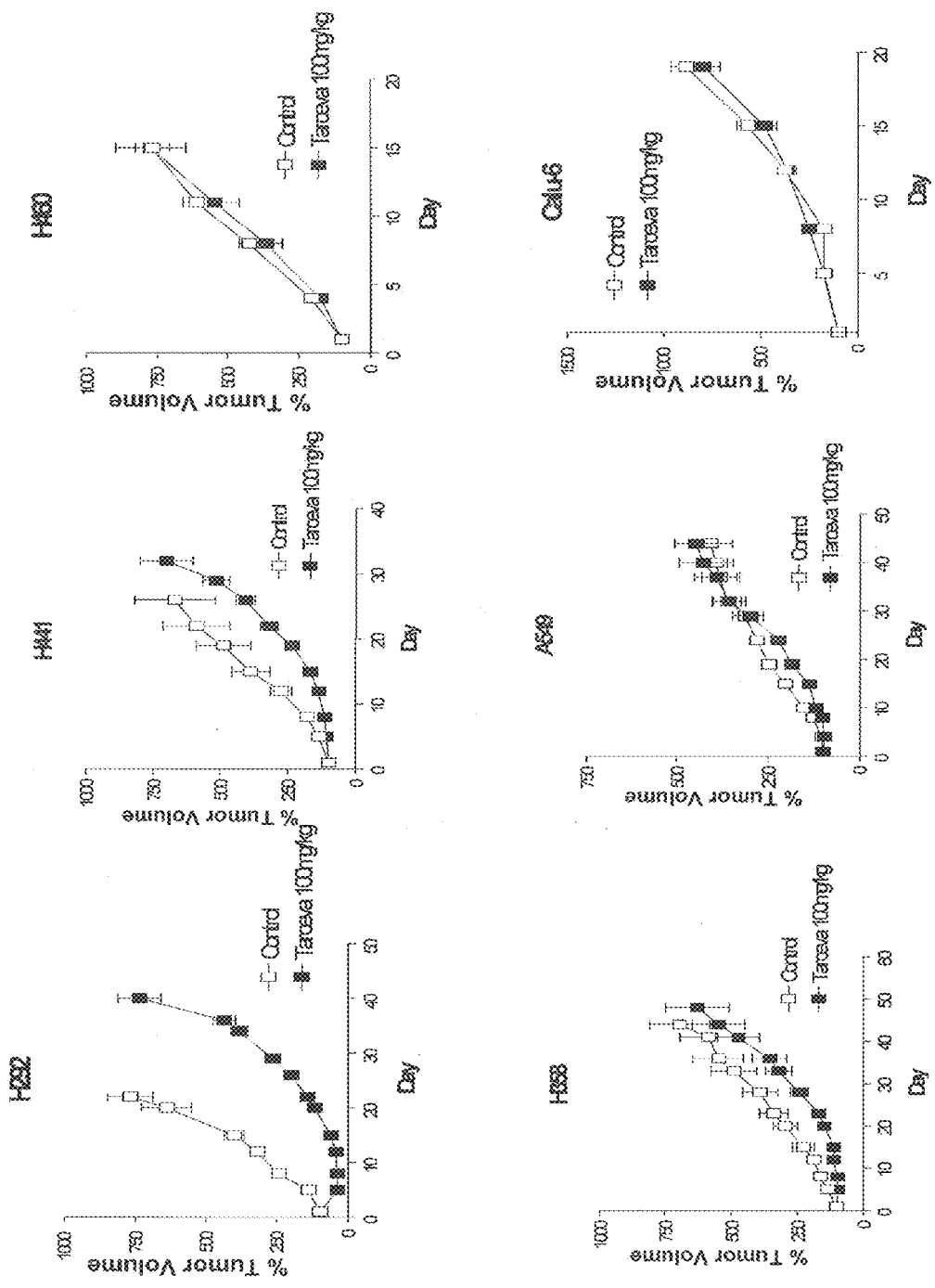
FIG. 1: In vivo activity of erlotinib against NSCLC xenografts.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The data presented in the Examples herein below demonstrate that tumor cells, such as NSCLC or pancreatic cancer cells, containing wild type EGFR, grown either in cell culture or in vivo, show a range of sensitivities to inhibition by EGFR kinase inhibitors, dependent on whether they have undergone an epithelial to mesenchymal transition (EMT). Prior to EMT, tumor cells are very sensitive to inhibition by EGFR kinase inhibitors such as erlotinib HCl(TARCEVA™), whereas tumor cells which have undergone an EMT are substantially less sensitive to inhibition by such compounds. The data indicates that the EMT may be a "general biological switch" that determines the level of sensitivity of tumors to EGFR kinase inhibitors. It is demonstrated that the level of sensitivity of tumors to EGFR kinase inhibitors can be assessed by determining the level of biomarkers expressed by a tumor cell that are characteristic for cells either prior to or subsequent to an EMT event. For example, high levels of tumor cell expression of epithelial biomarkers such as E-cadherin, indicative of a cell that has not yet undergone an EMT, correlate with high sensitivity to EGFR kinase inhibitors. Conversely, high levels of tumor cell expression of mesenchymal biomarkers such as vimentin or fibronectin, indicative of a cell that has undergone an EMT, correlate with low sensitivity to EGFR kinase inhibitors. Thus, these observations can form the basis of valuable new diagnostic methods for predicting the effects of EGFR kinase inhibitors on tumor growth, and give oncologists an additional tool to assist them in choosing the most appropriate treatment for their patients.

Accordingly, the present invention provides a method of predicting the sensitivity of tumor cell growth to inhibition by an EGFR kinase inhibitor, comprising: assessing the level of an epithelial biomarker expressed by a tumor cell; and predicting the sensitivity of tumor cell growth to inhibition by an EGFR kinase inhibitor, wherein high expression levels of tumor cell epithelial biomarkers correlate with high sensitivity to inhibition by EGFR kinase inhibitors. Preferred examples of epithelial biomarkers include E-cadherin and Brk (i.e. PTK-6) (see Table 1). Additional examples of epithelial biomarkers that can be utilized in the method of this invention include γ-catenin (i.e. junction plakoglobin), α-catenin (i.e. α1, α2, or α3 catenin), keratin 8, keratin 18, connexin 31, plakophilin 3, stratafin 1, laminin alpha-5 and ST14 (see Table 1).

The present invention also provides a method of predicting the sensitivity of tumor cell growth to inhibition by an EGFR kinase inhibitor, comprising: assessing the level of a mesenchymal biomarker expressed by a tumor cell; and predicting the sensitivity of tumor cell growth to inhibition by an EGFR kinase inhibitor, wherein high expression levels of tumor cell mesenchymal biomarkers correlate with low sensitivity to inhibition by EGFR kinase inhibitors. Preferred examples of mesenchymal biomarkers include vimentin and fibronectin (see Table 1). Additional examples of mesenchymal biomarkers that can be utilized in the method of this invention include fibrillin-1, fibrillin-2, collagen alpha-2(IV), collagen alpha-2(V), LOXL1, nidogen, C11orf9, tenascin, N-cadherin, and embryonal $EDB^+$fibronectin, tubulin alpha-3 and epimorphin (see Table 1).

In the practice of this invention, with preferred epithelial biomarkers, the level of expression in tumor cells that are sensitive to EGFR kinase inhibitors will generally be at such a high level that the biomarker will be very readily detectable, using for example a specific anti-biomarker antibody for detection. With preferred epithelial biomarkers, the level of expression in tumor cells that are relatively insensitive to EGFR kinase inhibitors will generally be at such a low level that the biomarker will be barely detectable, if at all, using similar procedures (e.g. in the data presented in the Examples herein below, compare E-cadherin levels between sensitive and relatively insensitive tumor cells in FIGS. 2B, 3 and 5).

However, for other less preferred epithelial biomarkers, the level of biomarker expression in tumor cells that are relatively insensitive to EGFR kinase inhibitors may be readily detectable, but nevertheless will be at a substantially lower level of expression than in tumor cells that are sensitive to EGFR kinase inhibitors (e.g., in the data presented in the Examples herein below, compare α-catenin levels for the relatively insensitive tumor cells H1703 or SW1573 with the sensitive tumor cells H441, H358, H322 and H292 in FIG. 2B).

Similarly, in the practice of this invention, with preferred mesenchymal biomarkers, the level of expression in tumor cells that are relatively insensitive to EGFR kinase inhibitors will generally be at such a high level that the biomarker will be very readily detectable, using for example a specific anti-biomarker antibody for detection. With preferred mesenchymal biomarkers, the level of expression in tumor cells that are relatively sensitive to EGFR kinase inhibitors will generally be at such a low level that the biomarker will be barely detectable, if at all, using similar procedures (e.g. in the data presented in the Examples herein below, compare fibronectin or vimentin levels between sensitive and relatively insensitive tumor cells in FIGS. 2B, 3 and 5).

Also, for other less preferred mesenchymal biomarkers, the level of biomarker expression in tumor cells that are relatively sensitive to EGFR kinase inhibitors may be readily detectable, but nevertheless will be at a substantially lower level of expression than in tumor cells that are relatively insensitive to EGFR kinase inhibitors.

For any given epithelial or mesenchymal biomarker, the range of expression level between tumor cells that are relatively insensitive to EGFR kinase inhibitors and those that are sensitive, can readily be assessed by one of skill in the art, for example by testing on a panel of tumor cells as described herein (e.g. FIG. 2B), or by testing in tumor biopsies from patients whose tumors display a range of sensitivities to an EGFR kinase inhibitor (e.g. TARCEVA™).

In the context of this invention, for a relatively small percentage of tumor cells that are relatively insensitive to EGFR kinase inhibitors, the methods described above for predicting the sensitivity of tumor cell growth to inhibition by an EGFR kinase inhibitor, comprising assessing the level of an epithelial or mesenchymal biomarker expressed by a tumor cell, in circumstances where only a single biomarker level is assessed, may falsely predict that tumor cell growth is sensitive to inhibition by an EGFR kinase inhibitor. For example, in the data presented in the Examples herein below, the levels of the epithelial biomarkers γ-catenin and α-catenin in H460 tumor cells, or the mesenchymal biomarker fibronectin in H1703 cells, falsely predict high sensitivity to EGFR kinase inhibitors (see FIG. 2B). Thus, based on such false predictions, a physician may be lead to treat a small number of patients with EGFR kinase inhibitors, and the tumor may not be sensitive to the inhibitor. However, for the vast majority of tumor cells (e.g. at least 90%, from the data presented in the Examples herein below), assessment of a single biomarker expression level would be expected to provide an accurate prediction of level of sensitivity to EGFR kinase inhibitors.

Furthermore, most importantly in the context of this invention, no tumor cells that are sensitive to EGFR kinase inhibitors have been found that when tested by the above methods (where only a single biomarker level is assessed) give a false prediction that tumor cell growth will be insensitive to inhibition by an EGFR kinase inhibitor. Thus, utilizing the testing methods described herein should never lead a physician to withhold treatment with an EGFR kinase inhibitor in cases where the patient may benefit from such treatment.

In addition, one of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgement of the attending physician to determine the most appropriate course of treatment for an individual patient, based upon test results, patient condition and history, and his own experience. There may even be occasions, for example, when a physician will choose to treat a patient with an EGFR kinase inhibitor even when a tumor is not predicted to be particularly sensitive to EGFR kinase inhibitors, based on data from diagnostic tests or from other criteria, particularly if all or most of the other obvious treatment options have failed, or if some synergy is anticipated when given with another treatment. The fact that the EGFR kinase inhibitors as a class of drugs are relatively well tolerated compared to many other anti-cancer drugs, such as more traditional chemotherapy or cytotoxic agents used in the treatment of cancer, makes this a more viable option.

Preferred examples of suitable epithelial biomarkers for use in this invention, such as E-cadherin, do not lead to any false predictions when used in the methods described above (where only a single biomarker level is assessed).

Furthermore, this invention also provides additional methods wherein simultaneous assessment of the expression level in tumor cells of more than one biomarker level is utilized. In preferred embodiments of these methods (described below) there is no level of false prediction, as is the case for some of the methods described above where a single biomarker expression level is assessed.

Accordingly, the present invention provides a method of predicting the sensitivity of tumor cell growth to inhibition by an EGFR kinase inhibitor, comprising: assessing the level of one or more (or a panel of) epithelial biomarkers expressed by a tumor cell; and predicting the sensitivity of tumor cell growth to inhibition by an EGFR kinase inhibitor, wherein simultaneous high expression levels of all of the tumor cell epithelial biomarkers correlates with high sensitivity to inhibition by EGFR kinase inhibitors. In one preferred embodiment of this method the epithelial biomarkers comprise E-cadherin and Brk, wherein simultaneous high expression level of the two tumor cell epithelial biomarkers correlates with high sensitivity to inhibition by EGFR kinase inhibitor. In another preferred embodiment of this method the epithelial biomarkers comprise E-cadherin and γ-catenin, wherein simultaneous high expression level of the two tumor cell epithelial biomarkers correlates with high sensitivity to inhibition by EGFR kinase inhibitor. Note that in the two latter preferred embodiments a high expression level of both biomarkers is required to indicate high sensitivity.

The present invention also provides a method of predicting the sensitivity of tumor cell growth to inhibition by an EGFR kinase inhibitor, comprising: assessing the level of one or more (or a panel of) mesenchymal biomarkers expressed by a tumor cell; and predicting the sensitivity of tumor cell growth to inhibition by an EGFR kinase inhibitor, wherein simultaneous low or undetectable expression levels of all of the tumor cell mesenchymal biomarkers correlates with high sensitivity to inhibition by EGFR kinase inhibitors. In one preferred embodiment of this method the mesenchymal biomarkers comprise vimentin and fibronectin, wherein simultaneous low or undetectable expression level of the two tumor cell mesenchymal biomarkers correlates with high sensitivity to inhibition by EGFR kinase inhibitor. Note that in the latter preferred embodiment a low or undetectable expression of both biomarkers is required to indicate high sensitivity.

The present invention also provides a method of predicting the sensitivity of tumor cell growth to inhibition by an EGFR kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an EGFR kinase inhibitor, wherein a high ratio of epithelial to mesenchymal biomarker expression levels correlates with high sensitivity to inhibition by EGFR kinase inhibitors. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

The present invention also provides a method of predicting the sensitivity of tumor growth to inhibition by an EGFR kinase inhibitor, comprising: assessing the level of one or more (or a panel of) epithelial biomarkers expressed by cells of the tumor; and predicting the sensitivity of tumor growth to inhibition by an EGFR kinase inhibitor, wherein simultaneous high expression levels of all of the tumor cell epithelial biomarkers correlates with high sensitivity to inhibition by EGFR kinase inhibitors. In one preferred embodiment of this method the epithelial biomarkers comprise E-cadherin and Brk, wherein simultaneous high expression level of the two tumor cell epithelial biomarkers correlates with high sensitivity to inhibition by EGFR kinase inhibitor. In another preferred embodiment of this method the epithelial biomarkers comprise E-cadherin and γ-catenin, wherein simultaneous high expression level of the two tumor cell epithelial biomarkers correlates with high sensitivity to inhibition by EGFR kinase inhibitor. Note that in the two latter preferred embodiments a high expression level of both biomarkers is required to indicate high sensitivity.

The present invention also provides a method of predicting the sensitivity of tumor growth to inhibition by an EGFR kinase inhibitor, comprising: assessing the level of one or more (or a panel of) mesenchymal biomarkers expressed by cells of the tumor; and predicting the sensitivity of tumor growth to inhibition by an EGFR kinase inhibitor, wherein simultaneous low or undetectable expression levels of all of the tumor cell mesenchymal biomarkers correlates with high sensitivity to inhibition by EGFR kinase inhibitors. In one preferred embodiment of this method the mesenchymal biomarkers comprise vimentin and fibronectin, wherein simultaneous low or undetectable expression level of the two tumor cell mesenchymal biomarkers correlates with high sensitivity to inhibition by EGFR kinase inhibitor. Note that in the latter preferred embodiment a low or undetectable expression of both biomarkers is required to indicate high sensitivity.

The present invention also provides a method of predicting the sensitivity of tumor growth to inhibition by an EGFR kinase inhibitor, comprising: assessing the level of an epithelial biomarker expressed by cells of the tumor; assessing the level of a mesenchymal biomarker expressed by cells of the tumor; and predicting the sensitivity of tumor growth to inhibition by an EGFR kinase inhibitor, wherein a high ratio of epithelial to mesenchymal biomarker expression levels correlates with high sensitivity to inhibition by EGFR kinase inhibitors. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

The present invention also provides a method of predicting whether a cancer patient is afflicted with a tumor that will respond effectively to treatment with an EGFR kinase inhibitor, comprising: assessing the level of one or more (or a panel of) epithelial biomarkers expressed by cells of the tumor; and predicting if the tumor will respond effectively to treatment with an EGFR kinase inhibitor, wherein simultaneous high expression levels of all of the tumor cell epithelial biomarkers correlates with a tumor that will respond effectively to treatment with an EGFR kinase inhibitor. In one preferred embodiment of this method the epithelial biomarkers comprise E-cadherin and Brk, wherein simultaneous high expression level of the two tumor cell epithelial biomarkers correlates with a tumor that will respond effectively to treatment with an EGFR kinase inhibitor. In another preferred embodiment of this method the epithelial biomarkers comprise E-cadherin and γ-catenin, wherein simultaneous high expression level of the two tumor cell epithelial biomarkers correlates with a tumor that will respond effectively to treatment with an EGFR kinase inhibitor. Note that in the two latter preferred embodiments a high expression level of both biomarkers is required to indicate a tumor that will respond effectively to treatment with an EGFR kinase inhibitor.

The present invention also provides a method of predicting whether a cancer patient is afflicted with a tumor that will respond effectively to treatment with an EGFR kinase inhibitor, comprising: assessing the level of one or more (or a panel of) mesenchymal biomarkers expressed by cells of the tumor; and predicting if the tumor will respond effectively to treatment with an EGFR kinase inhibitor, wherein simultaneous low or undetectable expression levels of all of the tumor cell mesenchymal biomarkers correlates with a tumor that will respond effectively to treatment with an EGFR kinase inhibitor. In one preferred embodiment of this method the mesenchymal biomarkers comprise vimentin and fibronectin, wherein simultaneous low or undetectable expression level of the two tumor cell mesenchymal biomarkers correlates with a tumor that will respond effectively to treatment with an EGFR kinase inhibitor. Note that in the latter preferred embodiment a low or undetectable expression of both biomarkers is required to indicate a tumor that will respond effectively to treatment with an EGFR kinase inhibitor.

The present invention also provides a method of predicting whether a cancer patient is afflicted with a tumor that will respond effectively to treatment with an EGFR kinase inhibitor, comprising: assessing the level of an epithelial biomarker expressed by cells of the tumor; assessing the level of a mesenchymal biomarker expressed by cells of the tumor; and predicting if the tumor will respond effectively to treatment with an EGFR kinase inhibitor, wherein a high ratio of epithelial to mesenchymal biomarker expression levels correlates with a tumor that will respond effectively to treatment with an EGFR kinase inhibitor. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

In the context of the methods of this invention, biomarkers expressed by a tumor cell can include molecular and cellular markers that indicate the transition state of the tumor cell. In a preferred embodiment the biomarker is an individual marker protein, or its encoding mRNA, characteristic of the particular transition state of the tumor, i.e. a tumor exhibiting epithelial or mesenchymal characteristics. In an alternative embodiment, in certain circumstances the biomarker may be a characteristic morphological pattern produced in the tumor cell by cellular macromolecules that is characteristic of either an epithelial or mesenchymal condition.

TABLE 1

Molecular Biomarker Gene Identification

| Human Biomarker | NCBI GeneID[1] | NCBI RefSeq[2] |
|---|---|---|
| E-cadherin | 999 | NP_004351 |
| Brk | 5753 | NP_005966 |
| γ-catenin | 3728 | NP_002221 |
| α1-catenin | 1495 | NP_001894 |
| α2-catenin | 1496 | NP_004380 |
| α3-catenin | 29119 | NP_037398 |
| keratin 8 | 3856 | NP_002264 |
| keratin 18 | 3875 | NP_000215 |
| connexin 31 | 2707 | NP_076872 |
| plakophilin 3 | 11187 | NP_009114 |
| stratifin 1 | 2810 | NP_006133 |
| laminin alpha-5 | 3911 | NP_005551 |
| ST14 | 19143 | NP_035306 |
| vimentin | 7431 | NP_003371 |
| fibronectin 1 | 2335 | NP_002017 |
| fibrillin-1 | 2200 | NP_000129 |
| fibrillin-2 | 2201 | NP_001990 |
| collagen alpha2(IV) | 1284 | NP_001837 |
| collagen alpha2(V) | 1290 | NP_000384 |
| LOXL1 | 4016 | NP_005567 |
| nidogen | 4811 | NP_002499 |
| C11orf9 | 745 | NP_037411 |
| tenascin | 3371 | NP_002151 |
| N-cadherin | 1000 | NP_001783 |

TABLE 1-continued

Molecular Biomarker Gene Identification

| Human Biomarker | NCBI GeneID[1] | NCBI RefSeq[2] |
|---|---|---|
| tubulin alpha-3 | 7846 | NP_006009 |
| epimorphin | 2054 | NP_919337 |

[1]The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2]The NCBI RefSeq (Reference Sequence) is an example of a sequence expressed by the biomarker gene.

Table 1 lists the genes coding for examples of molecular biomarkers that can be used in the practice of the methods of the invention described herein. The molecular biomarkers can include any product expressed by these genes, including variants thereof, e.g. expressed mRNA or protein, splice variants, co- and post-translationally modified proteins, polymorphic variants etc. In one embodiment the biomarker is the embryonal EDB+fibronectin, a splice variant expressed by the fibronectin 1 gene (Kilian, O. et al. (2004) Bone 35(6):1334-1345). A possible advantage of determining this fetal form of fibronectin is that one could readily distinguish mesenchymal-like tumors from surrounding stromal tissue. In an additional embodiment the biomarker can be an animal homologue of the human gene product (e.g. from dog, mouse, rat, rabbit, cat, monkey, ape, etc.).

In the methods described herein the tumor cell will typically be from a patient diagnosed with cancer, a precancerous condition, or another form of abnormal cell growth, and in need of treatment. The cancer may be lung cancer (e.g. non-small cell lung cancer (NSCLC)), pancreatic cancer, head and neck cancer, gastric cancer, breast cancer, colon cancer, ovarian cancer, or any of a variety of other cancers described herein below. The cancer is preferably one known to be potentially treatable with an EGFR kinase inhibitor.

In the methods of this invention, biomarker expression level can be assessed relative to a control molecule whose expression level remains constant throughout EMT, or when comparing tumor cells expressing either epithelial or mesenchymal transition states as indicated by molecular biomarkers (e.g. a "housekeeping" gene, such as GAPDH, β-actin, tubulin, or the like). Biomarker expression level can also be assessed relative to the other type of tumor cell biomarker (i.e. epithelial compared to mesenchymal), or to the biomarker level in non-tumor cells of the same tissue, or another cell or tissue source used as an assay reference.

In the methods of this invention, the level of an epithelial or mesenchymal biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, RT-PCR, in situ hybridization, cDNA microarray, or the like, as described in more detail below.

In the methods of this invention, the expression level of a tumor cell epithelial or mesenchymal biomarker is preferably assessed by assaying a tumor biopsy. However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

In the methods of this invention, the tumor cell can be a lung cancer tumor cell (e.g. non-small cell lung cancer (NSCLC)), a pancreatic cancer tumor cell, a breast cancer tumor cell, a head and neck cancer tumor cell, a gastric cancer tumor cell, a colon cancer tumor cell, an ovarian cancer tumor cell, or a tumor cell from any of a variety of other cancers as described herein below. The tumor cell is preferably of a type known to or expected to express EGFR kinase, as do all tumor cells from solid tumors. The EGFR kinase can be wild type or a mutant form.

In the methods of this invention, the EGFR kinase inhibitor can be any EGFR kinase inhibitor as described herein below, but is preferably 6,7-bis(2-methoxyethoxy)-4-quinazolin-4-yl]-(3-ethynylphenyl) amine (also known as erlotinib, OSI-774, or TARCEVA™ (erlotinib HCl), including pharmacologically acceptable salts or polymorphs thereof.

The following methods represent additional specific embodiments of the method of the invention.

The present invention provides a method of predicting the sensitivity of tumor growth to inhibition by an EGFR kinase inhibitor, comprising: assessing the level of an epithelial biomarker expressed by cells of the tumor; and predicting the sensitivity of tumor growth to inhibition by an EGFR kinase inhibitor, wherein high expression levels of tumor cell epithelial biomarkers correlate with high sensitivity of tumor growth to inhibition by EGFR kinase inhibitors.

The present invention provides a method of predicting the sensitivity of tumor growth to inhibition by an EGFR kinase inhibitor, comprising: assessing the level of a mesenchymal biomarker expressed by cells of the tumor; and predicting the sensitivity of tumor growth to inhibition by an EGFR kinase inhibitor, wherein high expression levels of tumor cell mesenchymal biomarkers correlate with low sensitivity of tumor growth to inhibition by EGFR kinase inhibitors.

The present invention provides a method of predicting whether a cancer patient is afflicted with a tumor that will respond effectively to treatment with an EGFR kinase inhibitor, comprising: assessing the level of an epithelial biomarker expressed by cells of the tumor; and predicting if the tumor will respond effectively to treatment with an EGFR kinase inhibitor, wherein high expression levels of tumor cell epithelial biomarkers correlate with a tumor that will respond effectively to treatment with an EGFR kinase inhibitor.

In the methods of this invention, the tumor can be a lung cancer tumor (e.g. non-small cell lung cancer (NSCLC)), a pancreatic cancer tumor, a breast cancer tumor, a head and neck cancer tumor, a gastric cancer tumor, a colon cancer tumor, an ovarian cancer tumor, or a tumor from any of a variety of other cancers as described herein below. The tumor is preferably of a type whose cells are known to or expected to express EGFR kinase, as do all solid tumors. The EGFR kinase can be wild type or a mutant form.

The present invention provides a method of predicting whether a cancer patient is afflicted with a tumor that will respond effectively to treatment with an EGFR kinase inhibitor, comprising: assessing the level of a mesenchymal biomarker expressed by cells of the tumor; and predicting if the tumor will respond effectively to treatment with an EGFR kinase inhibitor, wherein high expression levels of tumor cell mesenchymal biomarkers correlate with a tumor that will respond less effectively to treatment with an EGFR kinase inhibitor.

The present invention provides a method of predicting the sensitivity of tumor cell growth to inhibition by an EGFR kinase inhibitor comprising: determining the tumor cell level of at least one epithelial biomarker polypeptide; determining the tumor cell level of at least one control polypeptide; comparing the tumor cell level of at least one epithelial biomarker polypeptide to the tumor cell level of at least one control polypeptide; wherein a high ratio of tumor cell biomarker polypeptide to tumor cell control polypeptide indicates a high predicted sensitivity of tumor cell growth to inhibition by an EGFR kinase inhibitor. For this method, examples of useful epithelial biomarker polypeptides include E-cadherin, γ-catenin, keratin 8, keratin 18, connexin 31, plakophilin 3, stratafin 1, laminin alpha-5, ST14 and Brk.

The present invention provides a method of predicting the sensitivity of tumor cell growth to inhibition by an EGFR kinase inhibitor comprising: determining the tumor cell level of at least one epithelial biomarker polynucleotide that encodes an polypeptide; determining the tumor cell level of at least one control polynucleotide; comparing the tumor cell level of at least one epithelial biomarker polynucleotide that encodes a polypeptide to the tumor cell level of at least one control polynucleotide; wherein a high ratio of tumor cell biomarker polynucleotide to tumor cell control polynucleotide indicates a high predicted sensitivity of tumor cell growth to inhibition by an EGFR kinase inhibitor. For this method examples of polypeptides encoded by the epithelial biomarker polynucleotide include E-cadherin, γ-catenin, keratin 8, keratin 18, connexin 31, plakophilin 3, stratafin 1, laminin alpha-5, ST14 and Brk.

The present invention provides a method of predicting the sensitivity of tumor cell growth to inhibition by an EGFR kinase inhibitor comprising: determining the tumor cell level of at least one mesenchymal biomarker polypeptide; determining the tumor cell level of at least one control polypeptide; comparing the tumor cell level of at least one mesenchymal biomarker polypeptide to the tumor cell level of at least one control polypeptide; wherein a low ratio of tumor cell biomarker polypeptide to tumor cell control polypeptide indicates a high predicted sensitivity of tumor cell growth to inhibition by an EGFR kinase inhibitor. For this method, examples of useful mesenchymal biomarker polypeptides include vimentin and fibronectin.

The present invention provides a method of predicting the sensitivity of tumor cell growth to inhibition by an EGFR kinase inhibitor comprising: determining the tumor cell level of at least one mesenchymal biomarker polynucleotide that encodes an polypeptide; determining the tumor cell level of at least one control polynucleotide; comparing the tumor cell level of at least one mesenchymal biomarker polynucleotide that encodes an polypeptide to the tumor cell level of at least one control polynucleotide; wherein a low ratio of tumor cell biomarker polynucleotide to tumor cell control polynucleotide indicates a high predicted sensitivity of tumor cell growth to inhibition by an EGFR kinase inhibitor. For this method, examples of useful polypeptides encoded by the biomarker polynucleotide include vimentin and fibronectin.

The present invention provides a method of predicting the sensitivity of tumor cell growth to inhibition by an EGFR kinase inhibitor comprising: determining the tumor cell level of at least one epithelial biomarker polypeptide; determining a non-tumor cell level of at least one epithelial biomarker polypeptide; comparing the tumor cell level of at least one epithelial biomarker polypeptide to the non-tumor cell level of at least one epithelial biomarker polypeptide; wherein a high ratio of tumor cell biomarker polypeptide to non-tumor cell biomarker polypeptide indicates a high predicted sensitivity of tumor cell growth to inhibition by an EGFR kinase inhibitor. For this method, examples of useful epithelial biomarker polypeptide include E-cadherin, γ-catenin, keratin 8, keratin 18, connexin 31, plakophilin 3, stratafin 1, laminin alpha-5, ST14 and Brk.

The present invention provides a method of predicting the sensitivity of tumor cell growth to inhibition by an EGFR kinase inhibitor comprising: determining the tumor cell level of at least one epithelial biomarker polynucleotide that encodes an polypeptide; determining a non-tumor cell level of at least one epithelial biomarker polynucleotide that encodes an polypeptide; comparing the tumor cell level of at least one epithelial biomarker polynucleotide that encodes an polypeptide to the non-tumor cell level of at least one epithelial biomarker polynucleotide that encodes an polypeptide; wherein a high ratio of tumor cell biomarker polynucleotide to non-tumor cell biomarker polynucleotide indicates a high predicted sensitivity of tumor cell growth to inhibition by an EGFR kinase inhibitor. For this method, examples of useful polypeptides encoded by the epithelial biomarker polynucleotide include E-cadherin, γ-catenin, keratin 8, keratin 18, connexin 31, plakophilin 3, stratafin 1, laminin alpha-5, ST14 and Brk.

The present invention provides a method of predicting the sensitivity of tumor cell growth to inhibition by an EGFR kinase inhibitor comprising: determining the tumor cell level of at least one mesenchymal biomarker polypeptide; determining a non-tumor cell level of at least one mesenchymal biomarker polypeptide; comparing the tumor cell level of at least one mesenchymal biomarker polypeptide to the non-tumor cell level of at least one mesenchymal biomarker polypeptide; wherein a low ratio of tumor cell biomarker polypeptide to non-tumor cell biomarker polypeptide indicates a high predicted sensitivity of tumor cell growth to inhibition by an EGFR kinase inhibitor. For this method, examples of useful mesenchymal biomarker polypeptides include vimentin and fibronectin.

The present invention provides a method of predicting the sensitivity of tumor cell growth to inhibition by an EGFR kinase inhibitor comprising: determining the tumor cell level of at least one mesenchymal biomarker polynucleotide that encodes an polypeptide; determining a non-tumor cell level of at least one mesenchymal biomarker polynucleotide that encodes an polypeptide; comparing the tumor cell level of at least one mesenchymal biomarker polynucleotide that encodes an polypeptide to the non-tumor cell level of at least one mesenchymal biomarker polynucleotide that encodes an polypeptide; wherein a low ratio of tumor cell biomarker polynucleotide to non-tumor cell biomarker polynucleotide indicates a high predicted sensitivity of tumor cell growth to inhibition by an EGFR kinase inhibitor. For this method, examples of useful polypeptides encoded by the biomarker polynucleotide include vimentin and fibronectin.

The present invention provides a method of predicting the sensitivity of tumor cell growth to inhibition by an EGFR kinase inhibitor comprising: determining the tumor cell level of at least one epithelial biomarker polypeptide; determining the tumor cell level of at least one mesenchymal biomarker polypeptide; comparing the level of at least one epithelial biomarker polypeptide to the level of at least one mesenchymal biomarker polypeptide; wherein a high ratio of epithelial biomarker polypeptide to mesenchymal biomarker polypeptide indicates a high predicted sensitivity of tumor cell growth to inhibition by an EGFR kinase inhibitor. For this method, examples of useful epithelial biomarker polypeptides include E-cadherin, catenin, keratin 8, keratin 18, connexin 31, plakophilin 3, stratafin 1, laminin alpha-5, ST14 and Brk. For this method, examples of useful mesenchymal biomarker polypeptides include vimentin and fibronectin.

The present invention provides a method of predicting the sensitivity of tumor cell growth to inhibition by an EGFR kinase inhibitor comprising: determining the tumor cell level of at least one epithelial biomarker polynucleotide that encodes a polypeptide; determining the tumor cell level of at least one mesenchymal biomarker polynucleotide that encodes a polypeptide; (c) comparing the level of at least one epithelial biomarker polynucleotide to the level of at least one mesenchymal biomarker polynucleotide; wherein a high ratio of epithelial biomarker polynucleotide to mesenchymal biomarker polynucleotide indicates a predicted high sensitivity of tumor cell growth to inhibition by an EGFR kinase inhibitor. For this method, examples of useful polypeptides encoded by the epithelial biomarker polynucleotide include E-cadherin, γ-catenin, keratin 8, keratin 18, connexin 31, plakophilin 3, stratafin 1, laminin alpha-5, ST14 and Brk. For this method, examples of useful polypeptides encoded by the mesenchymal biomarker polynucleotide include vimentin and fibronectin.

The present invention provides a method of assessing whether a cancer patient is afflicted with a cancer that will respond effectively to treatment with an EGFR kinase inhibitor, the method comprising comparing: the level of expression of a mesenchymal biomarker in a patient sample; and the normal level of expression of the biomarker in a control non-cancer sample, wherein a significant increase in the level of expression of the mesenchymal biomarker in the patient sample over the normal level is an indication that the patient is afflicted with a cancer which is less likely to respond effectively to treatment with an EGFR kinase inhibitor. For this method, examples of useful mesenchymal biomarkers include vimentin and fibronectin, and nucleic acids encoding for these proteins.

The present invention provides a method of assessing whether a cancer patient is afflicted with a cancer that will respond effectively to treatment with an EGFR kinase inhibitor, the method comprising comparing: the level of expression of an epithelial biomarker in a patient sample; and the normal level of expression of the biomarker in a control non-cancer sample, wherein a significant decrease in the level of expression of the epithelial biomarker in the patient sample over the normal level is an indication that the patient is afflicted with a cancer which is less likely to respond effectively to treatment with an EGFR kinase inhibitor. For this method, examples of useful epithelial biomarkers include E-cadherin, γ-catenin, keratin 8, keratin 18, connexin 31, plakophilin 3, stratafin 1, laminin alpha-5, ST14 and Brk, and nucleic acids encoding for these proteins.

The present invention provides a method of assessing whether a cancer patient is afflicted with a cancer that will respond effectively to treatment with an EGFR kinase inhibitor, the method comprising comparing: the level of expression of an epithelial biomarker in a patient sample; and the level of expression of a mesenchymal biomarker in a patient sample, wherein a high ratio of the level of expression of the epithelial biomarker to the level of expression of the mesenchymal biomarker is an indication that the patient is afflicted with a cancer which is likely to respond effectively to treatment with an EGFR kinase inhibitor. For this method, examples of useful epithelial biomarkers include E-cadherin, γ-catenin, keratin 8, keratin 18, connexin 31, plakophilin 3, stratafin 1, laminin alpha-5, ST14 and Brk, and nucleic acids encoding for these proteins. For this method, examples of useful mesenchymal biomarkers include vimentin and fibronectin, and nucleic acids encoding for these proteins.

In any of the above methods referring to a patient sample, an example of such a sample can be a tumor biopsy.

The present invention provides a method of determining whether in a human subject a tumor will be responsive to treatment with an EGFR kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for one or more epithelial cell biomarker proteins or one or more epithelial cell biomarker protein-specific mRNAs; and (c) comparing the expression level in (b) to the level of biomarker expression in a normal control, or to the level of a control polypeptide or nucleic acid in the sample, wherein reduced expression of one or more epithelial cell biomarker proteins or one or more epithelial cell biomarker protein-specific mRNAs, with respect to the control level, indicates the presence in the human subject of a tumor which is less likely to respond effectively to treatment with an EGFR kinase inhibitor.

The present invention provides a method of determining whether in a human subject a tumor will be responsive to treatment with an EGFR kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for one or more mesenchymal cell biomarker proteins or one or more mesenchymal cell biomarker protein-specific mRNAs; and (c) comparing the expression level in (b) to the level of biomarker expression in a normal control, or to the level of a control polypeptide or nucleic acid in the sample, wherein increased expression of one or more mesenchymal cell biomarker proteins or one or more mesenchymal cell biomarker protein-specific mRNAs, with respect to the control level, indicates the presence in the human subject of a tumor which is less likely to respond effectively to treatment with an EGFR kinase inhibitor.

The present invention provides a method of determining the likelihood that a patient with a tumor will show relatively long survival benefit from therapy with an EGFR kinase inhibitor, comprising determining the level of one or more epithelial biomarkers in the cells of the tumor, comparing said level with the level of epithelial biomarker expression in a non-tumor control, or to the level of a control polypeptide or nucleic acid in the tumor sample, and determining whether the cells of the tumor contain a relatively high level of one or more epithelial biomarkers, a high level being indicative that a patient with a tumor will show relatively long survival benefit from therapy with an EGFR kinase inhibitor.

The present invention provides a method of determining the likelihood that a patient with a tumor will show relatively long survival benefit from therapy with an EGFR kinase inhibitor, comprising determining the level of one or more mesenchymal biomarkers in the cells of the tumor, comparing said level with the level of mesenchymal biomarker expression in a non-tumor control, or to the level of a control polypeptide or nucleic acid in the tumor sample, and determining whether the cells of the tumor contain a relatively low level of one or more mesenchymal biomarkers, a low level being indicative that a patient with a tumor will show relatively long survival benefit from therapy with an EGFR kinase inhibitor.

The present invention provides a method for determining for a patient with a tumor the likelihood that said patient will show relatively long survival benefit from therapy with an EGFR kinase inhibitor, comprising: determining the level of one or more epithelial biomarkers in the cells of the tumor, comparing said level with the level of epithelial biomarker expression in a non-tumor control, or to the level of a control polypeptide or nucleic acid in the tumor sample, and determining whether the cells of the tumor contain a relatively high level of one or more epithelial biomarkers; determining the level of one or more mesenchymal biomarkers in the cells of the tumor, comparing said level with the level of mesenchymal biomarker expression in a non-tumor control, or to the level of a control polypeptide or nucleic acid in the tumor sample, and determining whether the cells of the tumor contain a relatively low level of one or more mesenchymal biomarkers, wherein a high level of one or more epithelial biomarkers and a low level of one or more mesenchymal biomarkers is indicative that a patient with a tumor will show relatively long survival benefit from therapy with an EGFR kinase inhibitor.

The present invention provides a method of determining a prognosis for survival for a patient with a neoplastic condition in response to therapy with an EGFR kinase inhibitor, comprising: measuring the level of an epithelial biomarker associated with neoplastic cells, and comparing said level of epithelial biomarker to a non-neoplastic epithelial biomarker reference level, or to the level of a control polypeptide or nucleic acid associated with the neoplastic cells, wherein a decreased level of epithelial biomarker associated with the neoplastic cells correlates with decreased survival of said patient.

The present invention provides a method of determining a prognosis for survival for a patient with a neoplastic condition in response to therapy with an EGFR kinase inhibitor, comprising: measuring the level of an mesenchymal biomarker associated with neoplastic cells, and comparing said level of mesenchymal biomarker to a non-neoplastic mesenchymal biomarker reference level, or to the level of a control polypeptide or nucleic acid associated with the neoplastic cells, wherein an increased level of mesenchymal biomarker associated with the neoplastic cells correlates with decreased survival of said patient.

For assessment of tumor cell epithelial or mesenchymal biomarker expression, patient samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from a patient, or other patient sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g., fixation.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e. using reagents, such as different fluorescent probes, for each biomarker) or in individual reaction mixtures corresponding to one or more of the biomarkers.

The level of expression of a biomarker in normal (i.e. non-cancerous) human tissue can be assessed in a variety of ways. In one embodiment, this normal level of expression is assessed by assessing the level of expression of the biomarker in a portion of cells which appears to be non-cancerous, and then comparing this normal level of expression with the level of expression in a portion of the tumor cells. Alternately, and particularly as further information becomes available as a result of routine performance of the methods described herein, population-average values for normal expression of the biomarkers of the invention may be used. In other embodiments, the 'normal' level of expression of a biomarker may be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g. a tumor-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S, and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J. Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g. a mesenchymal biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^3H$. Standard radioactive isotopic labeling procedures include the chloramine T, lactoperoxidase and Bolton-Hunter methods for $^{125}I$ and reductive methylation for $^3H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

The invention also encompasses kits for detecting the presence of a biomarker protein or nucleic acid in a biological sample. Such kits can be used to determine if a subject is suffering from or is at increased risk of developing a tumor that is less susceptible to inhibition by EGFR kinase inhibitors. For example, the kit can comprise a labeled compound or agent capable of detecting a biomarker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a biomarker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

The present invention further provides a method for treating tumors or tumor metastases in a patient, comprising the steps of diagnosing a patient's likely responsiveness to an EGFR kinase inhibitor by assessing whether the tumor cells have undergone an epithelial-mesenchymal transition, by for example any of the methods described herein for determining the expression level of tumor cell epithelial and/or mesenchymal biomarkers, and administering to said patient a therapeutically effective amount of an EGFR kinase inhibitor. For this method, an example of a preferred EGFR kinase inhibitor would be erlotinib, including pharmacologically acceptable salts or polymorphs thereof. In this method one or more additional anti-cancer agents or treatments can be co-administered simultaneously or sequentially with the EGFR kinase inhibitor, as judged to be appropriate by the administering physician given the prediction of the likely responsiveness of the patient to an EGFR kinase inhibitor, in combination with any additional circumstances pertaining to the individual patient.

It will be appreciated by one of skill in the medical arts that the exact manner of administering to said patient of a therapeutically effective amount of an EGFR kinase inhibitor following a diagnosis of a patient's likely responsiveness to an EGFR kinase inhibitor will be at the discretion of the attending physician. The mode of administration, including dosage, combination with other anti-cancer agents, timing and frequency of administration, and the like, may be affected by the diagnosis of a patient's likely responsiveness to an EGFR kinase inhibitor, as well as the patient's condition and history. Thus, even patients diagnosed with tumors predicted to be relatively insensitive to EGFR kinase inhibitors may still benefit from treatment with such inhibitors, particularly in combination with other anti-cancer agents, or agents that may alter a tumor's sensitivity to EGFR kinase inhibitors.

The present invention further provides a method for treating tumors or tumor metastases in a patient, comprising the steps of diagnosing a patient's likely responsiveness to an EGFR kinase inhibitor by assessing whether the tumor cells have undergone an epithelial-mesenchymal transition, by for example any of the methods described herein for determining the expression level of tumor cell epithelial and/or mesenchymal biomarkers, identifying the patient as one who is likely to demonstrate an effective response to treatment with an EGFR kinase inhibitor, and administering to said patient a therapeutically effective amount of an EGFR kinase inhibitor.

The present invention further provides a method for treating tumors or tumor metastases in a patient, comprising the steps of diagnosing a patient's likely responsiveness to an EGFR kinase inhibitor by assessing whether the tumor cells have undergone an epithelial-mesenchymal transition, by for example any of the methods described herein for determining the expression level of tumor cell epithelial and/or mesenchymal biomarkers, identifying the patient as one who is less likely or not likely to demonstrate an effective response to treatment with an EGFR kinase inhibitor, and treating said patient with an anti-cancer therapy other than an EGFR kinase inhibitor.

The present invention further provides a method of identifying an epithelial biomarker whose expression level is predictive of the sensitivity of tumor cell growth to inhibition by an EGFR kinase inhibitor, comprising: (a) measuring the expression level of a candidate epithelial biomarker in a panel of tumor cells that displays a range of sensitivities to an EGFR kinase inhibitor, and (b) identifying a correlation between the expression level of said candidate epithelial biomarker in the tumor cells and the sensitivity of tumor cell growth to inhibition by the EGFR kinase inhibitor, wherein a correlation of high levels of the epithelial biomarker with high sensitivity of tumor cell growth to inhibition by the EGFR kinase inhibitor indicates that the expression level of said epithelial biomarker is predictive of the sensitivity of tumor cell growth to inhibition by an EGFR kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying a mesenchymal biomarker whose expression level is predictive of the sensitivity of tumor cell growth to inhibition by an EGFR kinase inhibitor, comprising: (a) measuring the expression level of a candidate mesenchymal biomarker in a panel of tumor cells that displays a range of sensitivities to an EGFR kinase inhibitor, and (b) identifying a correlation between the expression level of said candidate mesenchymal biomarker in the tumor cells and the sensitivity of tumor cell growth to inhibition by the EGFR kinase inhibitor, wherein a correlation of high levels of the mesenchymal biomarker with low sensitivity of tumor cell growth to inhibition by the EGFR kinase inhibitor indicates that the expression level of said mesenchymal biomarker is predictive of the lack of sensitivity of tumor cell growth to inhibition by an EGFR kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying an epithelial biomarker that is diagnostic for more effective treatment of a neoplastic condition with an EGFR kinase inhibitor, comprising: (a) measuring the level of a candidate epithelial biomarker in neoplastic cell-containing samples from patients with a neoplastic condition, and (b) identifying a correlation between the level of said candidate epithelial biomarker in the sample from the patient with the effectiveness of treatment of the neoplastic condition with an EGFR kinase inhibitor, wherein a correlation of high levels of the epithelial biomarker with more effective treatment of the neoplastic condition with an EGFR kinase inhibitor indicates that said epithelial biomarker is diagnostic for more effective treatment of the neoplastic condition with an EGFR kinase inhibitor.

The present invention further provides a method of identifying a mesenchymal biomarker that is diagnostic for less effective treatment of a neoplastic condition with an EGFR kinase inhibitor, comprising: (a) measuring the level of a candidate mesenchymal biomarker in neoplastic cell-containing samples from patients with a neoplastic condition, and (b) identifying a correlation between the level of said candidate mesenchymal biomarker in the sample from the patient with the effectiveness of treatment of the neoplastic condition with an EGFR kinase inhibitor, wherein a correlation of high levels of the mesenchymal biomarker with less effective treatment of the neoplastic condition with an EGFR kinase inhibitor indicates that said mesenchymal biomarker is diagnostic for less effective treatment of the neoplastic condition with an EGFR kinase inhibitor.

The effectiveness of treatment in the preceding methods can for example be determined by measuring the decrease in size of tumors present in the patients with the neoplastic condition, or by assaying a molecular determinant of the degree of proliferation of the tumor cells.

The present invention provides a method of identifying an epithelial biomarker that is diagnostic for increased survival of a patient with a neoplastic condition when treated with an EGFR kinase inhibitor, comprising: (a) measuring the level of the candidate epithelial biomarker in neoplastic cell-containing samples from patients with a neoplastic condition, and (b) identifying a correlation between the level of said candidate epithelial biomarker in the sample from the patient with the survival of that patient when treated with an EGFR kinase inhibitor, wherein the correlation of an epithelial biomarker with survival in said patients indicates said epithelial biomarker is diagnostic for increased survival of a patient with said neoplastic condition when treated with an EGFR kinase inhibitor.

The present invention provides a method of identifying a mesenchymal biomarker that is diagnostic for decreased survival of a patient with a neoplastic condition when treated with an EGFR kinase inhibitor, comprising: (a) measuring the level of the candidate mesenchymal biomarker in neoplastic cell-containing samples from patients with a neoplastic condition, and (b) identifying an inverse correlation between the level of said candidate mesenchymal biomarker in the sample from the patient with the survival of that patient when treated with an EGFR kinase inhibitor, wherein the inverse correlation of a mesenchymal biomarker with survival in said patients indicates said mesenchymal biomarker is diagnostic for decreased survival of a patient with said neoplastic condition when treated with an EGFR kinase inhibitor.

The present invention provides a method for the identification of an agent that enhances sensitivity of the growth of a tumor cell to an EGFR kinase inhibitor, said tumor cell having being characterized as one that has previously undergone an epithelial-mesenchymal transition, comprising contacting a sample of said tumor cells with an EGFR kinase inhibitor, contacting an identical sample of said tumor cells with an EGFR kinase inhibitor in the presence of a test agent, comparing the EGFR kinase inhibitor-mediated growth inhibition in the presence and absence of the test agent, and determining whether the test agent is an agent that enhances sensitivity of the growth of the tumor cell to an EGFR kinase inhibitor. For this method, an example of a preferred EGFR kinase inhibitor would be erlotinib, including pharmacologically acceptable salts or polymorphs thereof. In one embodiment of this method the sample of tumor cells can be cells in vitro, such as a tumor cell line or a primary tumor cell culture. In an alternative embodiment the sample of tumor cells can be cells in vivo, such as tumor cells in a mouse xenograft. In the latter embodiment, tumor cell growth can for example be determined by monitoring a molecular marker of growth or a gross measurement of tumor growth, e.g. tumor dimensions or weight.

Suitable test agents which can be tested in the preceding method include combinatorial libraries, defined chemical entities, peptide and peptide mimetics, oligonucleotides and natural product libraries, such as display (e.g. phage display libraries) and antibody products. Test agents may be used in an initial screen of, for example, 10 substances per reaction, and the substances of these batches which show inhibition or activation tested individually. Test agents may be used at a concentration of from 1 nM to 1000 µM, preferably from 1 µM to 100 µM, more preferably from 1 µM to 10 µM.

Agents which enhances sensitivity of the growth of a tumor cell to an EGFR kinase inhibitor which have been identified by the preceding methods can be used in the treatment of patients with cancers which are predicted to be less responsive to inhibition by EGFR kinase inhibitors (including lung cancer, pancreatic cancer, or any of the other cancer types described herein), and are an additional embodiment of this invention. Thus the present invention further provides a composition of matter comprising such an agent, which may be formulated and administered by any of the methods known in the art, including those described herein in relation to EGFR kinase inhibitors. Such agents that enhances sensitivity of the growth of a tumor cell to an EGFR kinase inhibitor may for example be agents that induce a mesenchymal to epithelial transition (MET), or that inhibit a specific cellular activity responsible for reduced sensitivity to EGFR kinase inhibitors, or induce a specific cellular activity that enhances sensitivity to EGFR kinase inhibitors. Examples of suitable agents include antagonists of EMT inducing agents, TGF-beta antagonists or TGF-beta receptor antagonists (for example: anti-TGF-beta and anti-TGF-beta receptor antibodies, 4-(4-Fluorophenyl)-2-(4-methylsulfinylphenyl)-5-(4-pyridyl)-1H-imidazole (SB 203580); 4-[4-(3,4-Methylenedioxyphenyl)-5-(2-pyridyl)-1H-imidazol-2-yl]-benzamide (SB431542); and similarly or more active analogues or homologues of such compounds), inhibitors of FAK, ILK, SRC, FYN or YES protein-tyrosine kinases, and calpain inhibitors.

The present invention further provides a method of treating tumors or tumor metastases in a patient, comprising administering to the patient a therapeutically effective amount of an EGFR kinase inhibitor and in addition, simultaneously or sequentially, one or more antagonists of an EMT inducing agent. In a preferred embodiment said tumor is first determined to have epithelial phenotype by the presence one or more epithelial biomarkers. In a particular embodiment, said EMT inducing agent is an anti-TGF-beta antibody, an anti-TGF-beta receptor antibody, 4-(4-Fluorophenyl)-2-(4-methylsulfinylphenyl)-5-(4-pyridyl)-1H-imidazole (SB 203580); or 4-[4-(3,4-Methylenedioxyphenyl)-5-(2-pyridyl)-1H-imidazol-2-yl]-benzamide (SB431542). In a particular embodiment, said EGFR antagonist is erlotinib.

The present invention further provides the preceding methods for treating tumors or tumor metastases in a patient, comprising administering to the patient a therapeutically effective amount of an EGFR kinase inhibitor and in addition, simultaneously or sequentially, one or more other cytotoxic, chemotherapeutic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (Cis P; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thioguanine (6TG), cytarabine (Ara-C), 5-fluorouracil (5-FU), capecitabine (e.g.XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides the preceding methods for treating tumors or tumor metastases in a patient, comprising administering to the patient a therapeutically effective amount of an EGFR kinase inhibitor and in addition, simultaneously or sequentially, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl) phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides the preceding methods for treating tumors or tumor metastases in a patient, comprising administering to the patient a therapeutically effective amount of an EGFR kinase inhibitor and in addition, simultaneously or sequentially, one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 4,530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606, 046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides the preceding methods for treating tumors or tumor metastases in a patient, comprising administering to the patient a therapeutically effective amount of an EGFR kinase inhibitor and in addition, simultaneously or sequentially, one or more tumor cell pro-apoptotic or apoptosis-stimulating agents.

The present invention further provides the preceding methods for treating tumors or tumor metastases in a patient, comprising administering to the patient a therapeutically effective amount of an EGFR kinase inhibitor and in addition, simultaneously or sequentially, one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors (e.g. BAY 43-9006, Onyx Pharmaceuticals/Bayer Pharmaceuticals); MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465, 449 and 6,541,481.

The present invention further provides the preceding methods for treating tumors or tumor metastases in a patient, comprising administering to the patient a therapeutically effective amount of an EGFR kinase inhibitor and in addition, simultaneously or sequentially, an anti-HER2 antibody or an immunotherapeutically active fragment thereof.

The present invention further provides the preceding methods for treating tumors or tumor metastases in a patient, comprising administering to the patient a therapeutically effective amount of an EGFR kinase inhibitor and in addition, simultaneously or sequentially, one or more additional antiproliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080, 769, 6,194,438, 6,258,824, 6,586,447, 6,071,935, 6,495,564, 6,150,377, 6,596,735 and 6,479,513, and International Patent Publication WO 01/40217.

The present invention further provides the preceding methods for treating tumors or tumor metastases in a patient, comprising administering to the patient a therapeutically effective amount of an EGFR kinase inhibitor and in addition, simultaneously or sequentially, a COX II (cyclooxygenase II) inhibitor. Examples of useful COX-II inhibitors include alecoxib (e.g. CELEBREX™), valdecoxib, and rofecoxib.

The present invention further provides the preceding methods for treating tumors or tumor metastases in a patient, comprising administering to the patient a therapeutically effective amount of an EGFR kinase inhibitor and in addition, simultaneously or sequentially, treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides the preceding methods for treating tumors or tumor metastases in a patient, comprising administering to the patient a therapeutically effective amount of an EGFR kinase inhibitor and in addition, simultaneously or sequentially, treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

As used herein, the term "patient" preferably refers to a human in need of treatment with an EGFR kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an EGFR kinase inhibitor.

In a preferred embodiment, the patient is a human in need of treatment for cancer, a precancerous condition or lesion, or other forms of abnormal cell growth. The cancer is preferably any cancer treatable, either partially or completely, by administration of an EGFR kinase inhibitor. The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

For purposes of the present invention, "co-administration of" and "co-administering" an EGFR kinase inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the EGFR kinase inhibitor, or in some combination thereof. Where the EGFR kinase inhibitor is administered to the patient at repeated intervals, e.g., during a standard course of treatment, the additional agent can be administered prior to, at the same time as, or subsequent to, each administration of the EGFR kinase inhibitor, or some combination thereof, or at different intervals in relation to the EGFR kinase inhibitor treatment, or in a single dose prior to, at any time during, or subsequent to the course of treatment with the EGFR kinase inhibitor.

The EGFR kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the EGFR kinase inhibitor can be administered in any effective manner known in the art, such as by oral, topical, intravenous, intra-peritoneal, intra-muscular, intra-articular, subcutaneous, intranasal, intra-ocular, vaginal, rectal, or intradermal routes, depending upon the type of cancer being treated, the type of EGFR kinase inhibitor being used (for example, small molecule, antibody, RNAi, ribozyme or antisense construct), and the medical judgment of the prescribing physician as based, e.g., on the results of published clinical studies.

The amount of EGFR kinase inhibitor administered and the timing of EGFR kinase inhibitor administration will depend on the type (species, gender, age, weight, etc.) and condition of the patient being treated, the severity of the disease or condition being treated, and on the route of administration. For example, small molecule EGFR kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based EGFR kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The EGFR kinase inhibitors and other additional agents can be administered either separately or together by the same or different routes, and in a wide variety of different dosage forms. For example, the EGFR kinase inhibitor is preferably administered orally or parenterally. Where the EGFR kinase inhibitor is erlotinib HCl (TARCEVA™), oral administration is preferable. Both the EGFR kinase inhibitor and other additional agents can be administered in single or multiple doses.

The EGFR kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous EGFR kinase inhibitors should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. In view of the teaching of the present invention, methods of preparing pharmaceutical compositions comprising an EGFR kinase inhibitor will be apparent from the above-cited publications and from other known references, such as Remington's Pharmaceutical Sciences, Mack Publishing Company, Easton, Pa., $18^{th}$ edition (1990).

For oral administration of EGFR kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous EGFR kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an EGFR kinase inhibitor in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. Such formulations are prepared in a conventional manner in accordance with standard veterinary practice.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors that include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or TARCEVA™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, TARCEVA™), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J.

W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

In the context of the methods of treatment of this invention, EGFR kinase inhibitors are used as a composition comprised of a pharmaceutically acceptable carrier and a non-toxic therapeutically effective amount of an EGFR kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an EGFR kinase inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the EGFR kinase inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an EGFR kinase inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An EGFR kinase inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise an EGFR kinase inhibitor compound in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols; oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical sue such as, for example, an aerosol, cream, ointment, lotion, dusting powder, or the like. Further, the compositions can be in a form suitable for use in transdermal devices. These formulations may be prepared, utilizing an EGFR kinase inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an EGFR kinase inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Academic Press, Inc. (e.g. ISBN 0-12-213585-7)), or as described in the many university and commercial websites devoted to describing experimental methods in molecular biology.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Introduction

Inhibitors of EGF receptor function have shown clinical utility and the definition of key EGF receptor signaling pathways which describe patient subsets most likely to benefit from therapy has become an important area of investigation. Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors has been controversial. In vitro and clinical studies have shown considerable variability between wt EGF receptor cell lines and tumors in their cellular responses to EGF receptor inhibition, which in part has been shown to derive from EGF receptor independent activation of the phosphatidyl inositol 3-kinase pathway, leading to the continued phosphorylation of the anti-apoptotic serine-threonine kinase Akt. The molecular determinants to alternative routes of PI3-kinase activation and consequent EGF receptor inhibitor insensitivity are an active area of investigation. Fir example the insulin-like growth factor-1 receptor (IGF-1 receptor), which strongly activates the PI3-kinase pathway, has been implicated in cellular resistance to EGF inhibitors. The roles of cell-cell and cell-adhesion networks, which can also exert survival signals through the PI3-kinase pathway in mediating insensitivity to selective EGF receptor inhibition are less clear and would be postulated to impact cell sensitivity to EGF receptor blockade. The ability of tumor cells to maintain growth and survival signals in the absence of adhesion to extracellular matrix or cell-cell contacts is important not only in the context of cell migration and metastasis but also in maintaining cell proliferation and survival in wound-like tumor environments where extracellular matrix is being remodeled and cell contact inhibition is diminished. Here we demonstrate that sensitivity of NSCLC and pancreatic cells to EGF receptor inhibition is conferred by an E-cadherin epithelial cell phenotype in which ErbB family member signaling was active. Conversely insensitivity to EGF receptor inhibition was mediated through an epithelial-mesenchymal transition (EMT) associated with the expression of vimentin and/or fibronectin.

Materials and Methods

Cell Culture and Preparation of Cell Extracts

The NSCLC lines with wt EGFR, H292, H358, H322, H441, A549, Calu6, H460, H1703 and SW1573 were cultured in the appropriate ATCC recommended supplemented media. Cell extracts were prepared by detergent lysis ((50 mM Tris-HCl, pH8, 150 mM NaCl, 1% NP-40, 0.5% NaDeoxycholate, 0.1% SDS) containing protease and phosphatase inhibitors. The soluble protein concentration was determined by micro-BSA assay (Pierce, Rockford, Ill.).

Protein Identification and Quantitation by LC-MS/MS Peptide Sequencing

Anti-phosphotyrosine immunoaffinity resins were prepared by covalent coupling to a solid support by standard methods. Freshly prepared immunoaffinity resins were used for each biological experiment to maximize binding and reduce carryover. Briefly, anti-phosphotyrosine antibodies were crosslinked to solid-support and non-covalently bound IgG removed by low pH elution. Fresh affinity resins were prepared for each biological experiment to avoid cross-contamination. Proteins isolated by anti-phosphotyrosine affinity selection were measured by iTRAQ labeling of tryptic peptides as previously described (Ross et al, 2004; Haley et al., 2004). Peptide masses and sequence information were determined by electrospray LC-MS/MS and database searching. Peptides with confidence levels of >=90% with scores of >=20 were considered, after which spectra were inspected manually. Peptide expression ratios were converted to $\log_2$ values and averaged to yield a single protein expression value for each time point (1, 4 and 24 hours) after erlotinib exposure (1 uM). Proteins were clustered by temporal $\log_2$ protein expression ratios using Euclidian hierarchical methods and self-organizing maps.

Immunoblot Analysis of NSCLC and Pancreatic Cell Line Extracts

Protein immunodetection was performed by electrophoretic transfer of SDS-PAGE separated proteins to nitrocellulose, incubation with antibody and chemiluminescent second step detection (PicoWest; Pierce, Rockford, Ill.). The antibodies included: E-Cadherin (Santa Cruz Biotechnology, Santa Cruz, Calif.; sc21791), α-catenin (sc9988), β-catenin (sc7963), γ-catenin (sc8415) and Brk (sc1188); Vimentin (BD Biosciences, San Jose, Calif.; BD550513) and Fibronectin (BD610077); GAPDH (AbCam, Cambridge, UK); Phospho-Akt (Cell Signaling, Beverly, Mass. #9271), Akt (CS, #9272), Phospho-p44/42 Map kinase$^{T202/Y204}$ (Erk1/2; CS #9101), Phospho-Src family$^{Y416}$ (CS #2101), Phospho-STAT3$^{Y705}$ (CS, #9131) and Phospho-S6$^{S235/S236}$ (CS, #2211); β-actin (Sigma, Saint Louis, Mo. #A5441). Antibodies further included: Phospho-Shc (Cell Signaling, #2434, Beverly, Mass.), Phospho-Paxillin (Cell Signaling, #2541), Phospho-Akt (Ser473 and Thr308) (Cell Signaling, #9271 and 9275), Phospho-HER2/ErbB2 (Cell Signaling, #2245), Phospho-Her3 (Tyr1289) (Cell Signaling #4791), Phospho-p44/42 Map kinase (Cell Signaling, #9101), Phospho-EGFR (Tyr845) (Cell Signaling, #2231), Phospho-EGFR (Tyr992) (Cell Signaling, #2235), Phospho-EGFR (Tyr1045) (Cell Signaling, #2237), EGFR (Cell Signaling, #2232), Phospho-p70 S6 kinase (Cell Signaling, #9205), Phospho-GSK-3alpha/beta (Cell Signaling, #9331), Phospho-EGFR (Tyr1068) (Cell Signaling, #2236), Phospho-Src family (Tyr416) (Cell Signaling #2101), phospho-SAPK/JNK (Thr183/Tyr185) (Cell Signaling #9251), phospho-STAT3 (Tyr705) (Cell Signaling #9131), ErbB2 (Cell Signaling #2242); ErbB4 (Cell Signaling 4795), PY20 (Exalpha Biologicals Inc.), Brk (Santa Cruz Biochemicals).

In vitro Pharmacology

On day 1, NSCLC cells were plated 3-5×10$^4$ cells/well in 96 well plates in their normal serum-containing media. After 24 h, erlotinib was added to the plates at a 10× concentration in a 10% DMSO/water solution to achieve a final assay concentration range from 20 µM to 8 nM. Dilutions were made in 3-fold steps. Final DMSO concentrations in each well was constant and did not exceed 1%. Following erlotinib addition, cells were replaced in the incubator and left for 72 h. On day 5, Cell-Titer Glo (Promega) was used to assess the effects on cell viability. Manufacturers instructions were followed for the assay. Experiments were conducted in triplicate to at least an n=3. Data was normalized as a percentage inhibition compared to DMSO only control wells and concentration-response analysis was performed using Prizm graphing software.

In vivo Pharmacology

Female CD-1 nu/nu mice (Charles River Laboratories) were implanted with harvested NSCLC tumor cells in a single subcutaneous site on the flank of the mice in the axillary region. Tumors were allowed to grow to 200±50 mm$^3$, at which time the animals were sorted into treatment groups of 8 animals per group based on weight (±1 g body weight) and tattooed on the tail for permanent identification. Tumor volumes and body weights were determined twice weekly. The tumor volume was determined by measuring in two directions with vernier calipers and calculated using the formula: Tumor volume=(length×width$^2$)/2. The data were plotted as the % change in mean values of tumor volume and body weight for each group. The tumor growth inhibition (% TGI) was determined as % TGI=100(1−W$_t$−W$_c$): where W$_t$ is the median tumor volume of the treated group at time x and W$_c$ is the median tumor volume of the control group at time x. TARCEVA™ was dosed in a 6% Captisol (CyDex, Inc) in WFI (Water for Injection) solution and all control animals were dosed with an equal volume of the vehicle. Tumor growth inhibition studies were dosed by oral gavage once a day for 14 days. Pharmacodynamic studies were dosed by oral gavage for 1-3 days with tumors from 4 control and 4 TARCEVA™ treated animals harvested and snap frozen in liquid nitrogen 4 hours after dosing on Days 1, 2 and 3.

Confocal Microscopy

Cells grown on glass coverslips for 24 hours were washed and fixed with 3.7% formaldehyde in PBS followed by permeabilization in 0.5% NP-40. The cells were washed, blocked with 5% BSA and incubated with primary antibody for 2 hours at room temperature and with diluted FITC-conjugated secondary antibody for 1 hour. Nuclei were stained with DAPI (300 nM for 5 min). The confocal images were captured using a spinning objective confocal microscope at 60× magnification.

Results

TABLE 2

Growth inhibition of wt EGF receptor tumor cell lines sensitive or relatively insensitive to erlotinib expressed as concentration (µM) required for half-maximal efficacy (EC$_{50}$) and maximum inhibition (%) by erlotinib. Tumor growth inhibition (TGI) is given for day 15 after xenograft exposure to erlotinib.

| Cell line | Max. Inhibition (%) | % TGI Day 15 | EC$_{50}$ Half Maximal | Classification |
|---|---|---|---|---|
| H292 | 69 | 85 | 0.1 | Sensitive |
| H322 | 80 | nd | 0.4 | Sensitive |
| H358 | 72 | 25 | 0.6 | Sensitive |
| H441 | 55 | 60 | 2 | Sensitive |
| A549 | 30 | 49 | 5 | Intermediate |
| H460 | 30 | 6 | 5 | Insensitive |
| Calu6 | 46 | 0 | >10 | Insensitive |
| H1703 | 30 | nd | 7 | Insensitive |
| SW1573 | 25 | nd | 9 | Insensitive |

NSCLC Lines Containing Wt EGF Receptor Display a Range of Sensitivities to Erlotinib in vitro NSCLC cell lines containing mutations in the catalytic domain of EGFR displayed hypersensitivity to treatment with the selective EGFR inhibitors erlotinib and gefitinib. It has been suggested that only those patients bearing such mutations would respond and/or show survival benefit from treatment with EGFR tyrosine kinase inhibitors. However, a randomized placebo controlled clinical trial conducted with erlotinib indicated that the survival rate of patients exposed to the drug was well in excess of the predicted occurrence of such mutations in the patient population. This suggested that, although mutations were an indicator of patient response, other factors were undoubtedly involved in conferring survival benefit.

Initially the receptor for epidermal growth factor (EGFR) was sequenced in 14 NSCLC cell lines. Sequence analysis demonstrated that the EGFR expressed in all of the cell lines of this study was wild-type with respect to two recently identified mutations (deletion and point mutations; data not shown). Having determined that the receptors were wild-type, the sensitivity of the panel of non-small cell lung cancer cell lines to erlotinib was assessed using a cell viability assay.

Analysis of erlotinib sensitivity in a range of human NSCLC cell lines, which are wild type for EGFR, indicated a wide range of sensitivity (Table 2; Griffin et al., 2005). We have thus broadly classified these cell lines into those that are relatively insensitive (H1703, SW1573, H460 and Calu6), those which show an intermediate sensitivity (A549) and those which are sensitive (H441, H358, H322 and H292) to erlotinib-mediated growth inhibition in vitro and in xenografts. These differences can be correlated in part to a failure of the relatively insensitive cell lines to show erlotinib-mediated inhibition of Akt/PKB phosphorylation (Griffin et al., 2005). A range of sensitivities of the cells to erlotinib was observed from cells lines ranging from the most sensitive (H292) through the least sensitive (H460). There were few correlations between tumor type and erlotinib sensitivity, although it is interesting to note that both of the bronchioalveolar carcinoma (BAC) derived cell lines (H358 and H322) showed a level of sensitivity to EGFR inhibition. Previous reports from clinical trials have suggested that of the population of NSCLC patients, those with BAC histologies tended to have a greater treatment benefit than other NSCLC patients. However, more BAC derived cell lines should be tested prior to making any conclusions. The data from the in vitro pharmacology experiments is summarized in Table 2. The concentration response curves were analyzed in two ways. Firstly in order to define the more traditionally accepted IC50 values (not shown), the curves have been fit in a 0-100% range. However, since erlotinib and other EGFR inhibitors may be described as cytostatic rather than cytotoxic, and therefore would therefore never be expected to achieve complete cell kill, it is questionable how relevant an IC50 value is. Indeed, even in the most sensitive lines a maximal efficacy of about 70-80% was the most observed. Therefore, an EC50 constraining the curves from 0-80% is a more relevant potency comparison.

In order to determine the relevance of the in vitro cell viability assay to in vivo efficacy, a selection of cell lines ranging from sensitive through insensitive in vitro were tested in mouse xenograft models. The data from these experiments are shown in FIG. 1 and Table 2. The correlation between in vitro sensitivity and in vivo sensitivity to erlotinib was striking. Those cells that were most sensitive in vitro, were also the most sensitive in vivo, with the rank order of sensitivities of all cell lines being identical between the two assays. Such a finding strongly supports the use of the in vitro assay as an initial guide for assessing erlotinib sensitivity in xenograft models. The cell lines chosen were picked for their range of sensitivities based on in vitro and in vivo activities. Although a somewhat subjective classification, two sensitive lines (H292 and H358), two intermediate (H441 and A549) and two insensitive (H460 and Calu-6) were selected. Despite its low sensitivity in vitro, A549 were classed as an intermediate cell line due to a low level of response in vivo. The principle aim of further study was to determine the molecular determinants of erlotinib sensitivity in these NSCLC cell lines.

Figure 2A:
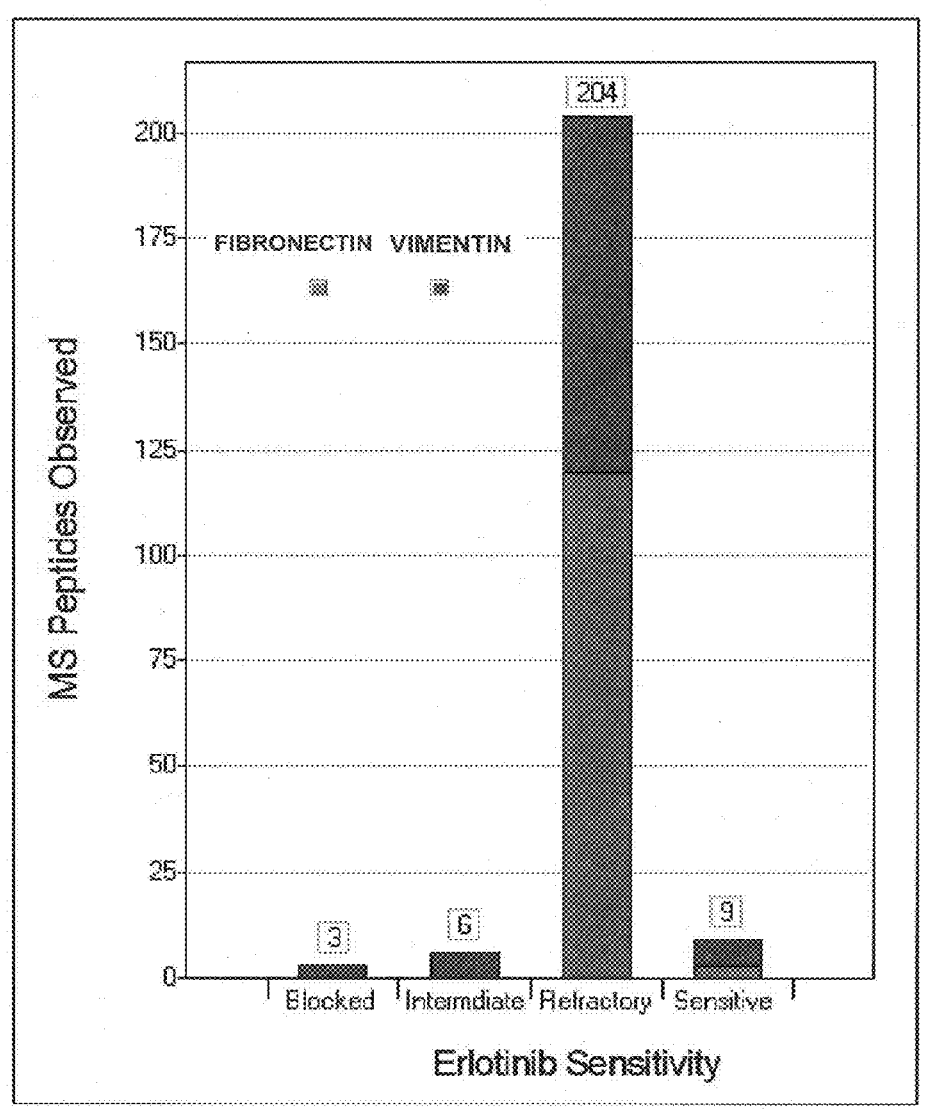
FIG. 2: A. Proteomic profiling of NSCLC lines, sensitive or relatively insensitive to EGFR kinase inhibition in vitro, showed markedly increased LC-MS/MS detection of vimentin and fibronectin peptides in cell lines relatively insensitive to erlotinib. B. NSCLC lines sensitive to EGF receptor inhibition express elevated levels of E-cadherin, with trends observed for γ- and α-catenins. E-cadherin immunoblots were performed with two distinct antibodies with similar results (data not shown). NSCLC lines relatively insensitive to growth inhibition by erlotinib expressed the mesenchymal proteins vimentin and/or fibronectin. No relationship between total EGF receptor protein expression and sensitivity was observed, though all lines tested expressed detectable EGF receptor. C. Confocal microscopy of NSCLC lines sensitive to growth inhibition by erlotinib, H292 and H441, showing membrane expression of E-cadherin, but not in the cell lines Calu6 and H1703 that are relatively insensitive to erlotinib. Conversely, the relatively insensitive lines Calu6 and H1703 expressed intermediate filament staining for vimentin, while the erlotinib sensitive lines H292 and H441 did not.

Changes in Epithelial and Mesenchymal Cell Markers Correlate with Sensitivity of NSCLC Cell Lines to Erlotinib Initially differences in protein tyrosine phosphorylation and complex formation between NSCLC lines sensitive or relatively insensitive to erlotinib in vitro and in xenograft models were measured. These experiments involved anti-phosphotyrosine affinity selection of cell lysates, tryptic digestion and protein identification based on LC-MS/MS fragment ion spectra. We observed a striking difference between the erlotinib sensitive and relatively insensitive NSCLC lines in the abnormal expression vimentin and or fibronectin (FIG. 2A). Typically vimentin and fibronectin expression are characteristic of mesenchymal cells and are only weakly or unexpressed in epithelial cell lineages. Vimentin expression was primarily found in H1703 and Calu6, while fibronectin expression was observed in H460 cells. These three NSCLC lines were relatively insensitive to growth inhibition by erlotinib in vitro (>10 uM $EC_{50}$) and in vivo (at 200 mg/kg orally qd). Little or no vimentin or fibronectin expression was found in the erlotinib sensitive NSCLC lines H292 and H358, the intermediate line A549 or in the two mutant EGF receptor cell lines H1650 and H1975.

Figure 2B:
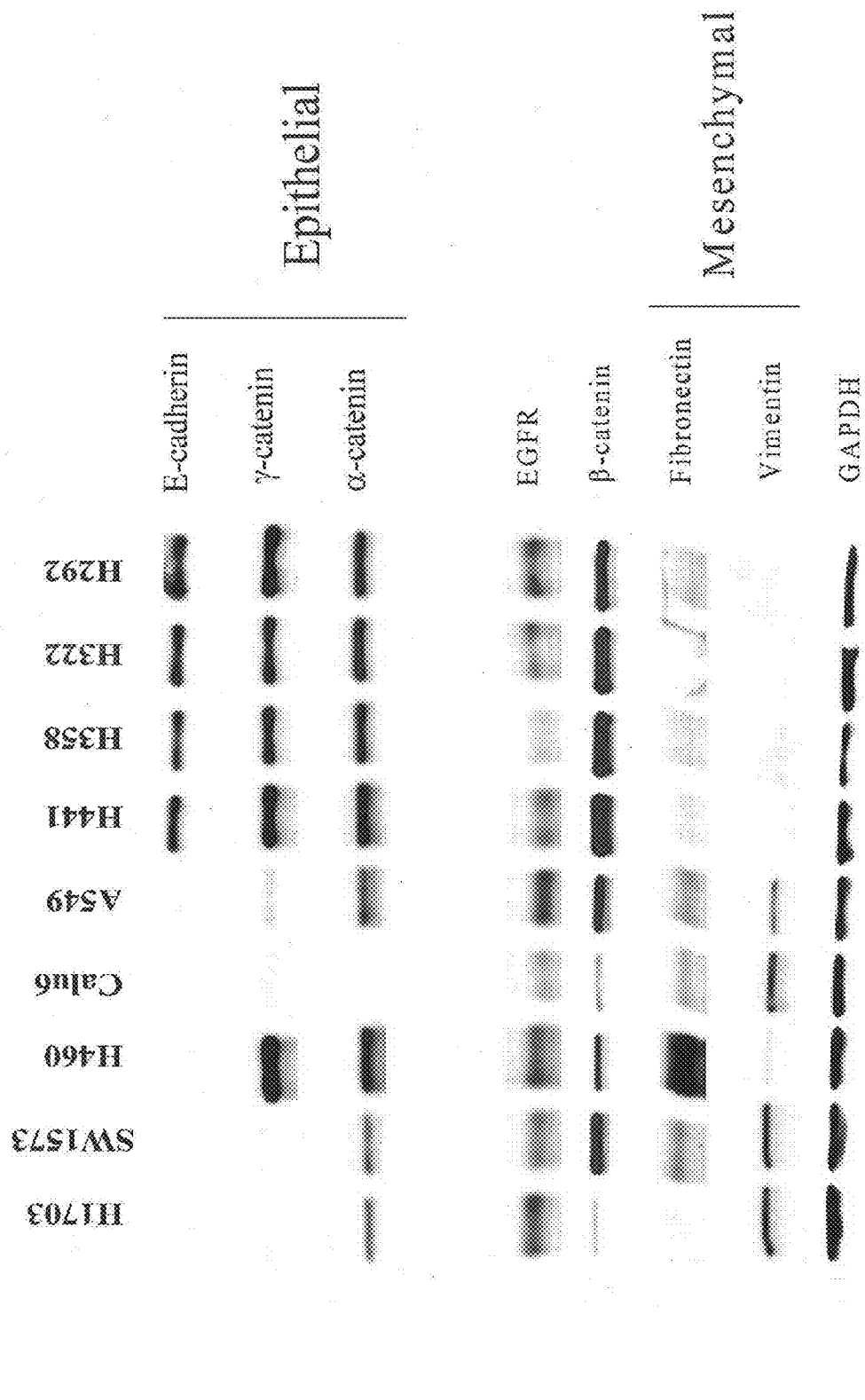

Based on the expression of mesenchymal proteins in NSCLC lines relatively insensitive to erlotinib, we analyzed protein extracts from the same panel of relatively insensitive and sensitive NSCLC cell lines for the presence or absence of markers characteristic of either epithelial or mesenchymal phenotypes (FIG. 2B). Strikingly, E-cadherin was detected in the sensitive cell lines (H441, H358, H322 and H292) but was absent in the relatively insensitive cell lines (H1703, SW1573, H460 and Calu6). The intermediately sensitive cell line A549 showed low but detectable expression. A similar loss of γ-catenin was observed in cells relatively insensitive to erlotinib, with the exception of H460. Therefore, the relatively insensitive cell lines appear to have lost expression of epithelial cell marker proteins. Next we asked whether these cell lines expressed the mesenchymal markers fibronectin and/or vimentin. The relatively insensitive cell lines clearly expressed either one or both of fibronectin and vimentin (FIG. 2B), whereas neither protein was detectable in cell lines sensitive to erlotinib. Interestingly the intermediately sensitive cell line A549 again showed low but detectable levels of both proteins. However, confocal microcopy experiments (results not shown) using immunostaining with antibodies specific for E-cadherin and vimentin indicated that the A549 cell culture used appears to be a mixed population of cells since no dual staining of cells was observed. This could also explain the somewhat variable results obtained with this cell line, and is consistent with its intermediate sensitivity to erlotinib.

Figure 2C:
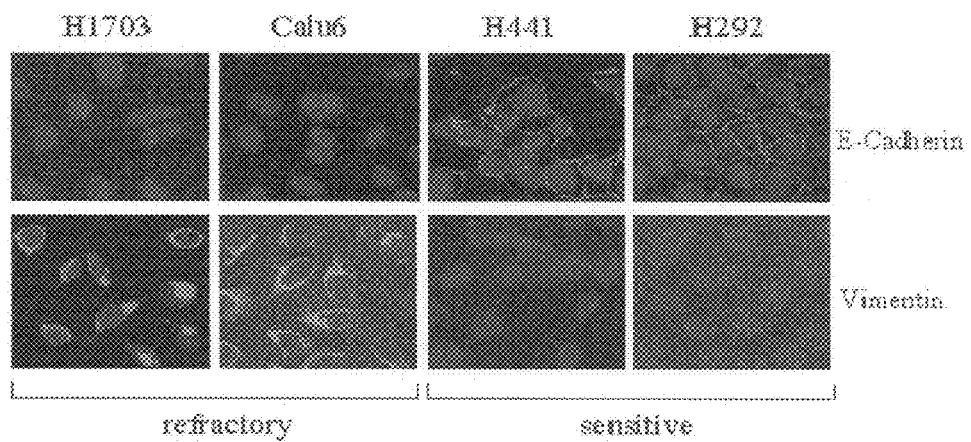

The changes in cell-lineage markers were further analyzed in two relatively insensitive and two sensitive cell lines by confocal microscopy after immunostaining with antibodies toward E-cadherin and vimentin (FIG. 2C). No E-cadherin staining could be detected in either H1703 or Calu6 cells (FIG. 2C, panels 1 and 2), whereas all of these cells could be stained for vimentin (FIG. 2C, panels 5 and 6). The reverse was true for the sensitive cell lines H441 and H292, with clear E-cadherin staining on the membrane of these cells (FIG. 2C, panels 3 and 4) but no visible vimentin staining (FIG. 2C, panels 7 and 8). Taken together these data indicate that NSCLC cells which were relatively insensitive to growth inhibition by erlotinib appeared to have undergone transition to a more mesenchymal cell type and expressed either vimentin or fibronectin. In contrast cell lines that were sensitive to growth inhibition by erlotinib maintained an epithelial phenotype and expressed E-cadherin.

Figure 3:
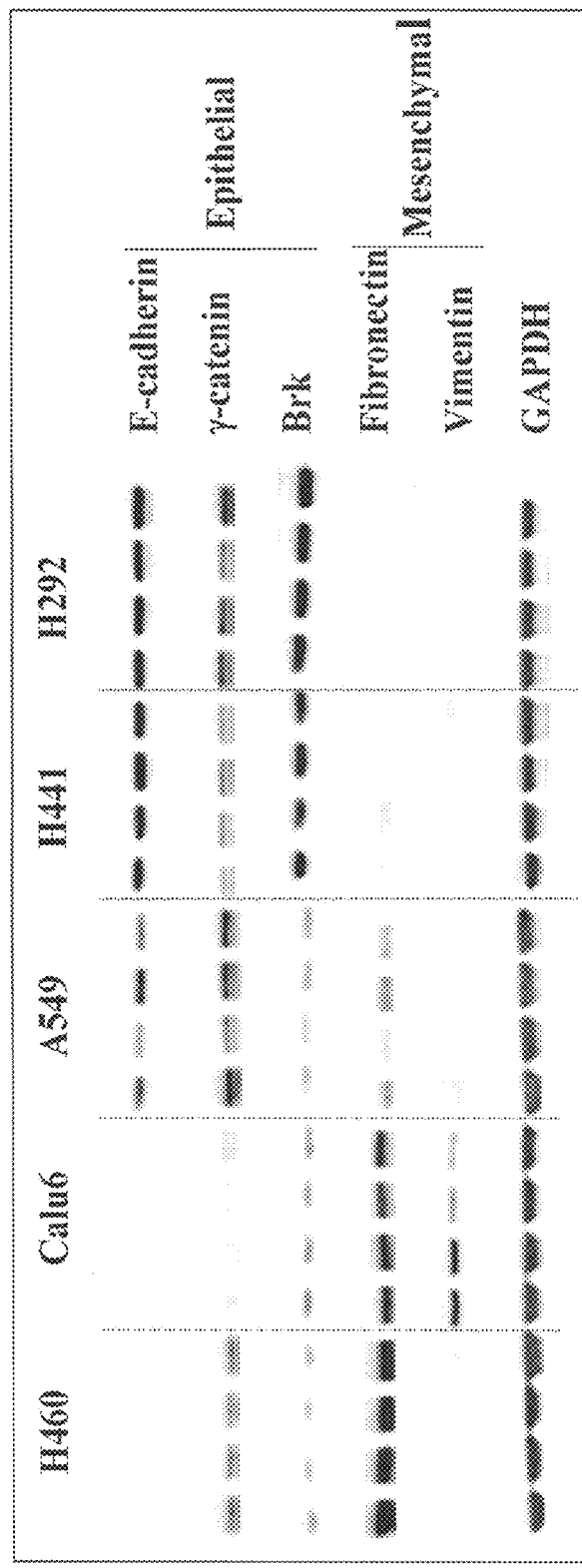
FIG. 3: NSCLC lines were grown as subcutaneous xenografts in SCID mice to a volume of ~500 mm$^3$, excised and flash frozen in liquid nitrogen (4 animals per cell line). Tumor tissue was pulverized while frozen, subjected to detergent lysis and SDS-PAGE as described and immunoblots probed with antibodies to E-cadherin, γ-catenin, Brk, fibronectin, vimentin, and GAPDH. Consistent with in vitro results, E-cadherin expression was restricted to erlotinib sensitive lines and fibronectin to relatively insensitive lines.

Erlotinib Sensitivity Correlates with Maintenance of Epithelial Markers During Tumor Growth In Vivo Tumors xenografts derived from NSCLC cell lines grown in mice displayed a similar degree of erlotinib sensitivity to that observed for the respective cell line in vitro. We therefore wished to examine whether the protein markers identified in vitro were also predictive of erlotinib sensitivity in vivo. Protein extracts were prepared from 3 independent tumor xenografts grown from H460, Calu6, A549, H441 and H292 cells. Immunoblotting of extracts indicated that E-cadherin was not detectably expressed in the xenografts derived from the H460 and Calu6 cells that are relatively insensitive to erlotinib, was expressed at low levels in xenografts derived from the A549 cells of intermediate sensitivity and expressed at high levels in H441 and H292 cell lines sensitive to erlotinib (FIG. 3). A similar result was observed on analysis of γ-catenin levels. In contrast xenograft samples derived from Calu6 expressed fibronectin and vimentin (Calu6) or fibronectin alone (H460), a result consistent with that obtained from in vitro cell cultures (FIG. 2B). H441 and H292 derived xenograft extracts showed little or no expression of either fibronectin or vimentin. These in vivo results further support the in vitro data and indicate that the presence of these protein markers is not an artifact of cell culture. Further, they support the hypothesis that erlotinib sensitivity may be restricted to cells with an epithelial phoenotype and that cells which have undergone EMT become less dependent upon EGFR signaling for cell proliferation and survival.

Figure 4:
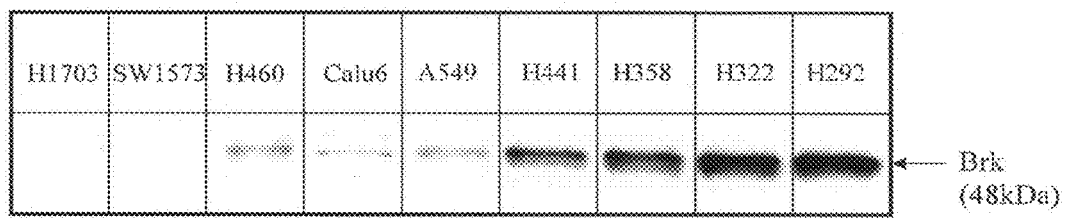
FIG. 4: Immunoblot showing higher Brk expression levels in NSCLC cell lines that are most sensitive to EGFR kinase inhibition.

Expression of Brk in NSCLC Cell Lines that are Relatively Insensitive or Sensitive to EGF Receptor Inhibition The results of these experiments led to the working hypothesis that erlotinib sensitivity is determined by the ability of the compound to inhibit Akt signaling. Following this hypothesis the question arises as to what is unique about these cells that allows the EGFR pathway to so significantly impact cellular Akt signaling. Recent papers by (REFS) have suggested an interesting potential link between EGFR and Akt signaling, which may or may not involve heterodimerization with other Her members such as ErbB3, involving the non receptor tyrosine kinase Brk (also known as PTK6). It was of interest therefore to determine whether there may be any relationship between Brk expression in sensitive and insensitive erlotinib lines, thus providing a rationale for why EGFR inhibition is so intricately linked to Akt in sensitive compared to insensitive. FIG. 4 shows Western blot analysis of a number of lines from the NSCLC panel, and their respective expression of Brk protein. Interestingly there is a very good correlation between Brk levels and erlotinib sensitivity in so far as high Brk expression equates to higher erlotinib sensitivity and absence, or lower expression, of Brk tends to characterize insensitive lines.

Figure 5:
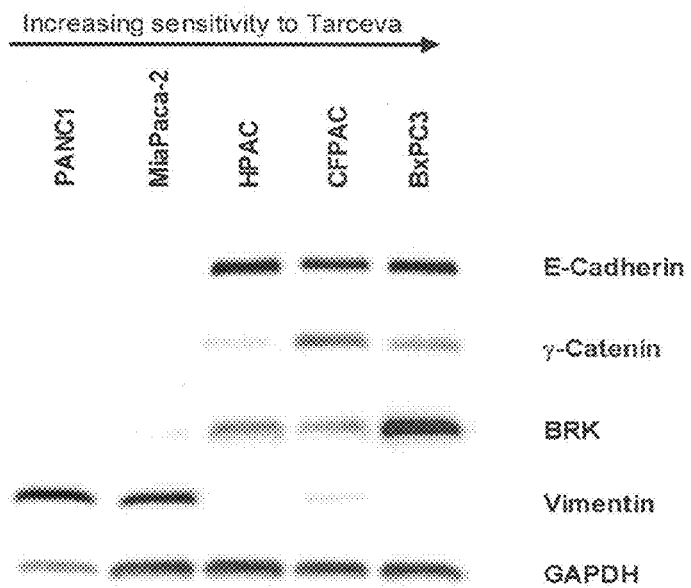
FIG. 5: A) Pancreatic cell lines sensitive to EGF receptor inhibition express elevated levels of the epithelial cell junction proteins E-cadherin and γ-catenin. The mesenchymal marker vimentin was most abundant in the insensitive PANC 1 cells. B) Confocal microscopy of a pancreatic cell line sensitive to growth inhibition by erlotinib, BxPC3, showing membrane expression of E-cadherin, but not in the cell line MiaPaca2, that is relatively insensitive to erlotinib. Conversely, the relatively insensitive line MiaPaca2 expressed intermediate filament staining for vimentin, while the erlotinib sensitive line BxPC3 did not.
Figure 5:
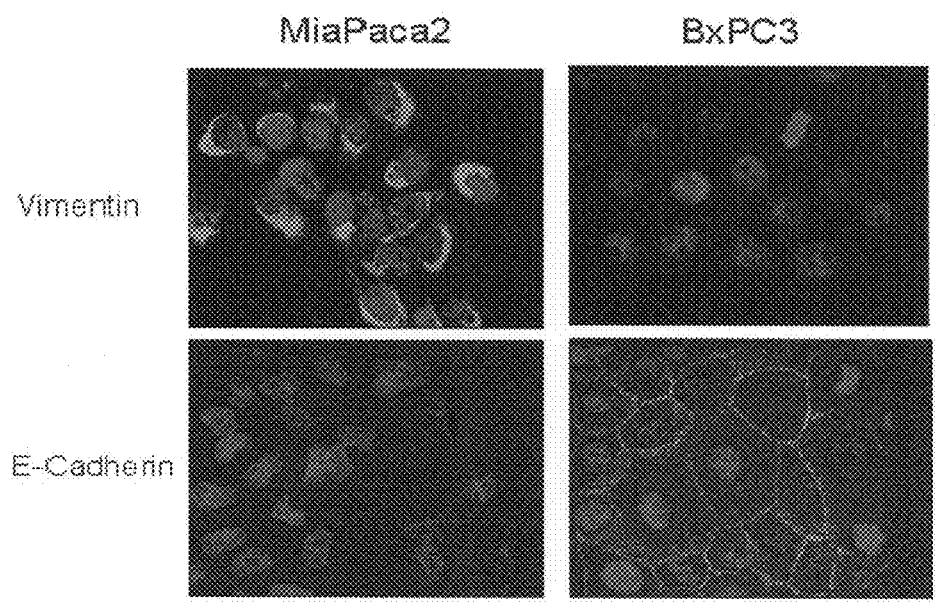

Analysis of EMT Markers is Predictive of Erlotinib Sensitivity of Pancreatic Cell Lines in Culture We next extended these studies to ask whether these observations would be applicable to other cancer cell types. As erlotinib has shown efficacy in Phase III combination studies with gemcitabine in pancreatic cancer, we examined the sensitivity of pancreatic cell lines to growth inhibition by erlotinib in vitro and their expression of epithelial and mesenchymal lineage markers. Consistent with data in NSCLC, pancreatic cell lines sensitive to erlotinib expressed E-cadherin but not vimentin or fibronectin, while pancreatic lines that are relatively insensitive to erlotinib had lost E-cadherin expression and gained vimentin and/or fibronectin expression (FIG. 5). These results were observed both by immunoblot (FIG. 5A) and confocal fluorescence microscopy studies (FIG. 5B).

Patients with Tumors Expressing High Levels of E-Cadherin have Greater Time to Disease Progression when Treated with Erlotinib+Chemotherapy Compared to Chemotherapy Treatment Alone Samples from patients who participated in a randomized, double-blinded phase III clinical trial referred to as Tribute were analyzed for E-cadherin expression by Immunohistochemistry (IHC). Tribute studied 1,079 patients at approximately 150 centers in the United States having histological confirmed NSCLC who had not received prior chemotherapy comparing erlotinib+chemotherapy (carboplatin/paclitaxel) with chemotherapy alone. Patients received paclitaxel (200 mg/m$^2$ 3 hour i.v. infusion) followed by carboplatin (AUC=6 mg/ml×minute infused over 15-30 minutes using Calvert formula) with or without erlotinib (100 mg/day p.o. escalated to 150 mg/day for tolerant patients). Tumor samples, formalin-fixed paraffin-embedded blocks or unstained slides, from 87 patients in the Tribute trial were immunostained to detect E-cadherin expression. Staining intensity was scored as 0, 1+, 2+ and 3+ with 65 of the 87 samples having >=2 staining intensity and 22 had <=1 staining intensity.

Immunohistochemistry for E-cadherin was performed on formalin-fixed paraffin embedded tissue sections assembled in a tissue microarray. Following deparaffinization, antigen retrieval was performed by pretreating with Target Retrieval Solution at 110 degrees C. for 20 min (DakoCytomation, Carpenteria Calif.). The pretreated sections were then incubated with primary mouse monoclonal IgG2 antibody against E-cadherin (clone 36, Pharmingen) at a concentration of 1 microgram/ml for 60 min at ambient temperature. Primary antibody bound to the sections was detected using biotinylated horse anti-mouse IgG, and visualized using the avidin-biotin peroxidase complex technique (Vectastain ABC Elite, Vector Laboratories) and diaminobenzidine as chromagen.

Figure 6A:
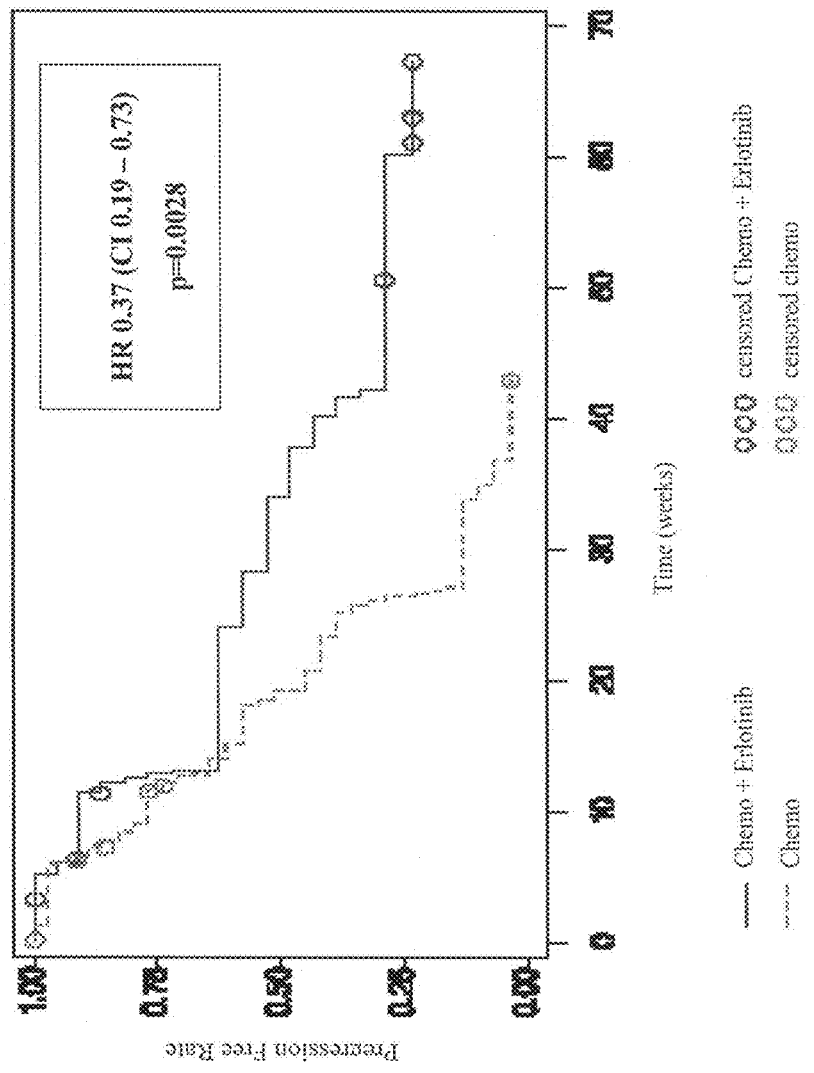
FIG. 6a: Kaplan-Meier curve illustrating time to disease progression (TTP) is longer for patients receiving erlotinib in combination with chemotherapy compared to patients receiving chemotherapy only whose tumors with E-cadherin staining intensity of >=2.
Figure 6B:
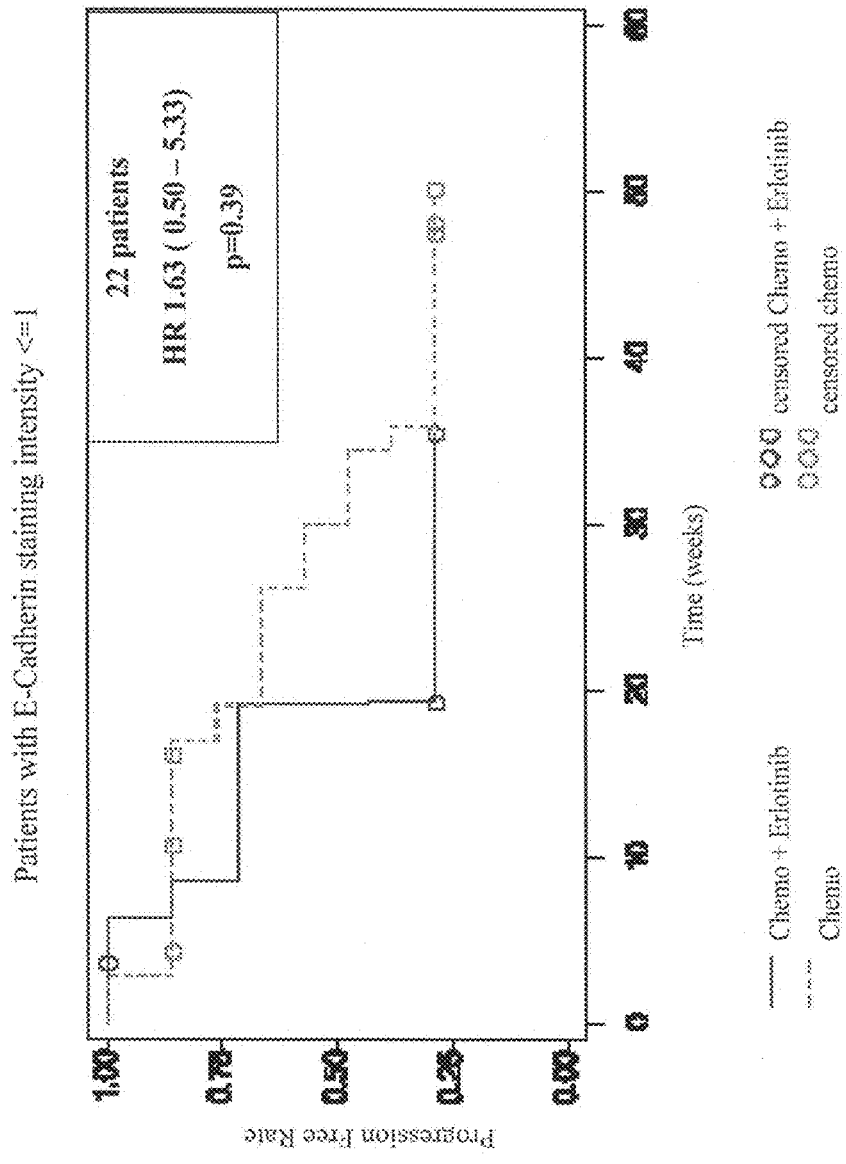
FIG. 6b: Kaplan-Meier curve illustrating time to disease progression (TTP) is not extended for patients having tumor E-cadherin staining intensity of <=1 who are treated with erlotinib in combination with chemotherapy compared to patients receiving chemotherapy alone.

It was determined that patients whose tumors stained for high levels of membrane and cytoplasmic E-cadherin exhibited significantly longer time to disease progression (TTP) when treated with the combination of erlotinib and chemotherapy compared to chemotherapy alone (34.0 weeks v. 19.3 weeks, p=0.0028). The results are provided in table 2 and are illustrated by the Kaplan-Meier curve in FIG. 6a. Conversely, patients whose tumors had low membrane and cytoplasmic E-cadherin expression (staining intensity of <=1) did not have a significant difference in TTP for the two treatment groups which is illustrated by the Kaplan-Meier curve in FIG. 6b.

TABLE 2

Time to Progression by E-cadherin staining for erlotinib + chemotherapy and chemotherapy alone treatment groups

| | Intensity >= 2 | | Intensity <= 1 | |
| --- | --- | --- | --- | --- |
| | Chemo | Erlotinib + chemo | Chemo | Erlotinib + chemo |
| N | 37 | 28 | 14 | 8 |
| Patients who progressed | 31 (83.8%) | 16 (57.1%) | 8 (57.1%) | 5 (62.5%) |
| Censored patients | 6 (16.2%) | 12 (42.9%) | 6 (42.9%) | 3 (37.5%) |
| Median time (wk) | 19.3 | 34.0 | 30.0 | 19.1 |
| 95% CI | (12.9, 25.7) | (13.1, 42.1) | (19.1, -) | (8.6, -) |
| P-Value (Logrank) | | 0.0028 | | 0.3976 |
| Hazard ratio (HR) | | 0.37 | | 1.63 |
| 95% CI for HR | | (0.19, 0.73) | | (0.50, 5.33) |

Conclusion

The loss of E-cadherin expression and the acquisition of a more mesenchymal phenotype has been shown to correlate with poor prognosis in multiple epithelial-derived solid tumors. The loss of E-cadherin and to a lesser extent γ-catenin and Brk correlated with cellular and xenograft insensitivity to EGF receptor inhibition. Conversely the cellular acquisition of mesenchymal markers, vimentin, fibronectin or fibrillin correlates with a loss of sensitivity to EGF receptor inhibitors. We clearly show that a partial or complete epithelial to mesenchymal transition negatively impacts cellular responses to EGF receptor inhibitors in vitro and in xenografts and serves a diagnostic for patients most likely to benefit from EGF receptor kinase inhibitors and anti-EGF receptor antibody therapies.

Abbreviations

EGF, epidermal growth factor; EMT, epithelial to mesenchymal transition; NSCLC, non-small cell lung carcinoma; HNSCC, head and neck squamous cell carcinoma; CRC, colorectal cancer; MBC, metastatic breast cancer; EGFR, epidermal growth factor receptor; Brk, Breast tumor kinase (also known as protein tyrosine kinase 6 (PTK6)); LC, liquid chromatography; MS, mass spectrometry; IGF-1, insulin-like growth factor-1; TGFα, transforming growth factor alpha; HB-EGF, heparin-binding epidermal growth factor; LPA, lysophosphatidic acid; TGFα, transforming growth factor alpha; $IC_{50}$, half maximal inhibitory concentration; pY, phosphotyrosine; wt, wild-type; PI3K, phosphatidyl inositol-3 kinase; GAPDH, Glyceraldehyde 3-phosphate dehydrogenase.

Incorporation by Reference

All patents, published patent applications and other references disclosed herein are hereby expressly incorporated herein by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating non-small-cell lung, pancreatic, colorectal, hepatocellular or breast tumors or tumor metastases in a patient comprising administering to said patient a therapeutically effective amount of erlotinib when it has been determined that tumor cells of the patient have simultaneous high expression levels of two or more epithelial protein biomarkers selected from the group consisting of (a) E-cadherin and γ-catenin, (b) E-cadherin and α-catenin, (c) E-cadherin and Brk, (d) E-cadherin, γ-catenin, and Brk, (e) E-cadherin, γ-catenin, and α-catenin, as observed in epithelia carcinoma cells, and indicative that the tumor cells from the patient will have high sensitivity to erlotinib, and that the patient is thus likely to be responsive to treatment with erlotinib.

2. The method of claim 1, wherein one or more additional anti-cancer agents are co-administered simultaneously or sequentially with erlotinib.

3. A method for treating non-small-cell lung, pancreatic, colorectal, hepatocellular or breast tumors or tumor metastases in a patient comprising administering to said patient a therapeutically effective amount of erlotinib when it has been determined that tumor cells of the patient have simultaneous low or undetectable expression levels of the mesenchymal protein biomarkers vimentin and fibronectin, as observed in epithelial carcinoma cells, and indicative that the tumor cells from the patient will have high sensitivity to erlotinib, and that the patient is thus likely to be responsive to treatment with erlotinib.

4. The method of claim 3, wherein one or more additional anti-cancer agents are co-administered simultaneously or sequentially with erlotinib.

5. A method for treating non-small-cell lung, pancreatic, colorectal, hepatocellular or breast tumors or tumor metastases in a patient comprising administering to said patient a therapeutically effective amount of erlotinib when it has been determined that tumor cells of the patient have a high ratio of epithelial to mesenchymal protein biomarker expression levels when the epithelial and mesenchymal biomarkers are selected from the group consisting of (a) E-cadherin and vimentin, (b) E-cadherin and fibronectin, and (c) γ-catenin and fibronectin, as observed in epithelial carcinoma cells, and indicative that the tumor cells from the patient will have high sensitivity to erlotinib, and that the patient is thus likely to be responsive to treatment with erlotinib.

6. The method of claim 5, wherein one or more additional anti-cancer agents are co-administered simultaneously or sequentially with erlotinib.

* * * * *